United States Patent
Kawamura et al.

(10) Patent No.: US 9,353,027 B2
(45) Date of Patent: *May 31, 2016

(54) ORGANIC ELECTROLUMINESCENT ELEMENT USING PYRENE DERIVATIVE

(75) Inventors: Masahiro Kawamura, Sodegaura (JP);
Yuichiro Kawamura, Sodegaura (JP);
Yumiko Mizuki, Sodegaura (JP);
Hiroyuki Saito, Sodegaura (JP);
Hirokatsu Ito, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 394 days.

This patent is subject to a terminal disclaimer.

(21) Appl. No.: 13/499,303

(22) PCT Filed: Dec. 20, 2010

(86) PCT No.: PCT/JP2010/007363
§ 371 (c)(1),
(2), (4) Date: Mar. 30, 2012

(87) PCT Pub. No.: WO2011/077691
PCT Pub. Date: Jun. 30, 2011

(65) Prior Publication Data
US 2012/0187826 A1 Jul. 26, 2012

(30) Foreign Application Priority Data
Dec. 21, 2009 (JP) ................................ 2009-289735

(51) Int. Cl.
| H01L 51/54 | (2006.01) |
|---|---|
| C07C 15/38 | (2006.01) |
| H01L 51/00 | (2006.01) |
| C09K 11/06 | (2006.01) |
| H05B 33/10 | (2006.01) |
| H01L 51/50 | (2006.01) |

(52) U.S. Cl.
CPC ................. *C07C 15/38* (2013.01); *C09K 11/06* (2013.01); *H01L 51/0054* (2013.01); *H05B 33/10* (2013.01); *C07C 2103/50* (2013.01); *C09K 2211/1007* (2013.01); *C09K 2211/1011* (2013.01); *H01L 51/5012* (2013.01)

(58) Field of Classification Search
CPC .... C07C 15/38; C07C 2103/50; C09K 11/06; C09K 2211/1007; C09K 2211/1011; H01L 51/0054; H01L 51/5012; H05B 33/10
See application file for complete search history.

(56) References Cited

U.S. PATENT DOCUMENTS

| 2003/0157365 A1 | 8/2003 | Kinoshita et al. | |
|---|---|---|---|
| 2004/0076853 A1* | 4/2004 | Jarikov | 428/690 |
| 2005/0079385 A1 | 4/2005 | Nomura et al. | |
| 2006/0134456 A1 | 6/2006 | Ikeda et al. | |
| 2006/0154107 A1 | 7/2006 | Kubota et al. | |
| 2007/0243411 A1 | 10/2007 | Takashima et al. | |
| 2008/0012475 A1 | 1/2008 | Oyamada et al. | |
| 2009/0009073 A1 | 1/2009 | Ikeda et al. | |
| 2009/0009074 A1 | 1/2009 | Ikeda et al. | |
| 2009/0079331 A1* | 3/2009 | Igawa et al. | 313/504 |
| 2009/0096356 A1 | 4/2009 | Murase et al. | |
| 2009/0128009 A1 | 5/2009 | Heil et al. | |
| 2009/0278446 A1* | 11/2009 | Igawa | C07C 13/567 313/504 |

(Continued)

FOREIGN PATENT DOCUMENTS

| JP | 2001-118682 | 4/2001 |
|---|---|---|
| JP | 2002-63988 | 2/2002 |

(Continued)

OTHER PUBLICATIONS

U.S. Appl. No. 13/389,294, filed Feb. 7, 2012, Mizuki, et al.

(Continued)

*Primary Examiner* — Dawn L. Garrett

(74) *Attorney, Agent, or Firm* — Oblon, McClelland, Maier & Neustadt, L.L.P.

(57) ABSTRACT

An organic electroluminescence device includes a pair of electrodes and an organic compound layer therebetween. The organic compound layer includes an emitting layer. The emitting layer includes a pyrene derivative represented by formula (1), such that a content of the pyrene derivative in the emitting layer is 50 to 100 wt %. $Ar_1$ and $Ar_2$ are independently a substituted or unsubstituted aryl group having 6 to 30 ring carbon atoms. $X_1$ and $X_3$ to $X_8$ are a hydrogen atom. $X_2$ is a substituted or unsubstituted aryl group having 6 to 30 ring carbon atoms, provided that $Ar_1$ or $Ar_2$ is different from $X_2$. In a case where any of $Ar_1$, $Ar_2$, and $X_2$ is the aryl group having a substituent, the substituent is independently an alkyl group, a cycloalkyl group, an aryl group, a silyl group, or a cyano group.

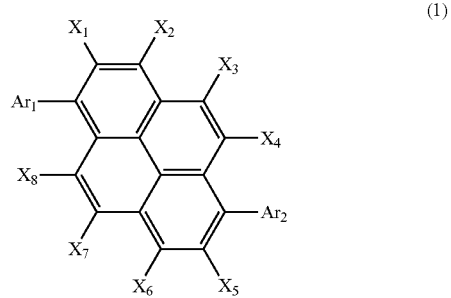

(1)

11 Claims, No Drawings

(56) References Cited

U.S. PATENT DOCUMENTS

| | | | | |
|---|---|---|---|---|
| 2012/0168733 | A1* | 7/2012 | Mizuki et al. | 257/40 |
| 2012/0248420 | A1* | 10/2012 | Mizuki et al. | 257/40 |

FOREIGN PATENT DOCUMENTS

| | | |
|---|---|---|
| JP | 2003-234190 | 8/2003 |
| JP | 2004-43349 | 2/2004 |
| JP | 2004-75567 | 3/2004 |
| JP | 2005-126431 | 5/2005 |
| JP | 2008-78362 | 4/2008 |
| JP | 2008-159843 | 7/2008 |
| JP | 2008-545762 | 12/2008 |
| JP | 2009-35516 | 2/2009 |
| WO | WO 2005/115950 A1 | 12/2005 |
| WO | WO 2006/057325 A1 | 6/2006 |
| WO | WO 2007/029798 A1 | 3/2007 |
| WO | WO 2007/100010 A1 | 9/2007 |

OTHER PUBLICATIONS

U.S. Appl. No. 13/389,142, filed Mar. 13, 2012, Mizuki, et al.
International Search Report issued Mar. 29, 2011 in Application No. PCT/JP2010/007363.
U.S. Appl. No. 14/871,055, filed Sep. 30, 2015, Kawamura, et al.

* cited by examiner

ORGANIC ELECTROLUMINESCENT ELEMENT USING PYRENE DERIVATIVE

TECHNICAL FIELD

The invention relates to an organic electroluminescence device using a pyrene derivative. More particularly, the invention relates to an organic electroluminescence device having high blue color purity and a long life.

BACKGROUND ART

An organic electroluminescence (EL) device is a promising solid-state emitting type inexpensive and large full-color display device, and has been extensively developed. In general, an organic EL device includes an emitting layer and a pair of opposing electrodes holding the emitting layer therebetween. When an electric field is applied between the electrodes, electrons are injected from the cathode and holes are injected from the anode. Further, the electrons recombine with the holes in the emitting layer to produce an excited state, and energy is emitted as light when the excited state returns to the ground state.

Conventional organic EL devices have a high driving voltage as compared with inorganic emitting diodes, and have a low luminance and a low luminous efficiency. Further, since their properties tend to deteriorate significantly, practical application thereof has not been realized yet. Although gradual improvements have been made on organic EL devices recently, further prolongation in life, improvement in luminous efficiency or the like are demanded.

The performance of an organic EL device has been gradually improved with improvements in emitting materials for an organic EL device. Improvement in luminous efficiency and prolongation in life of an organic EL device are important subjects leading to lowering in consumption in power and improvement of durability. Although improvement has been attained as a result of various studies, further improvement has been required.

As the emitting material of the emitting layer, a material which emits each color (red, green and blue, for example) has been developed. For example, a pyrene derivative is disclosed in Patent Documents 1 to 8 as a blue-emitting material.

However, there is a problem that the pyrene derivatives disclosed in Patent Documents 1 to 8 are not sufficient in respect of blue color purity and lifetime.

RELATED ART DOCUMENTS

Patent Documents

Patent Document 1: JP-A-2002-63988
Patent Document 2: JP-A-2001-118682
Patent Document 3: JP-A-2003-234190
Patent Document 4: JP-A-2004-75567
Patent Document 5: JP-A-2004-43349
Patent Document 6: JP-A-2005-126431
Patent Document 7: WO05/115950
Patent Document 8: WO06/057325

SUMMARY OF THE INVENTION

The invention relates to an organic EL device having a high blue color purity and has a long life.

According to the invention, the following organic EL device is provided.

1. An organic electroluminescence device comprising a pair of electrodes and one or more organic compound layers therebetween, the one or more organic compound layers comprising an emitting layer,
wherein the emitting layer comprises a pyrene derivative represented by the following formula (1) and the content of the pyrene derivative in the emitting layer is 50 to 100 wt %;

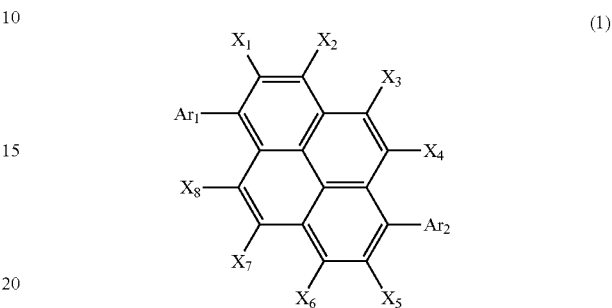

(1)

wherein $Ar_1$ and $Ar_2$ are independently a substituted or unsubstituted aryl group having 6 to 30 carbon atoms that form a ring (hereinafter referred to as "ring carbon atoms"),
$X_1$ to $X_8$ are independently a hydrogen atom, a substituted or unsubstituted aryl group having 6 to 30 ring carbon atoms, a substituted or unsubstituted alkyl group, or a substituted or unsubstituted cycloalkyl group, and at least one of $X_1$ to $X_8$ is a substituted or unsubstituted aryl group having 6 to 30 ring carbon atoms, provided that $Ar_1$ or $Ar_2$ is different from a substituted or unsubstituted aryl group having 6 to 30 ring carbon atoms of $X_1$ to $X_8$.

2. The organic electroluminescence device according to 1 wherein one of $X_1$ to $X_8$ is a substituted or unsubstituted aryl group having 6 to 30 ring carbon atoms, and the remainder of $X_1$ to $X_8$ are all a hydrogen atom.

3. The organic electroluminescence device according to 1 or 2 wherein $X_2$ is a substituted or unsubstituted aryl group having 6 to 30 ring carbon atoms, and $X_1$ and $X_3$ to $X_8$ are a hydrogen atom.

4. The organic electroluminescence device according to any of 1 to 3 wherein $Ar_1$ and $Ar_2$ are independently a substituted or unsubstituted phenyl group.

5. The organic electroluminescence device according to 4 wherein the substituted or unsubstituted phenyl group is a substituent represented by the following formula (2);

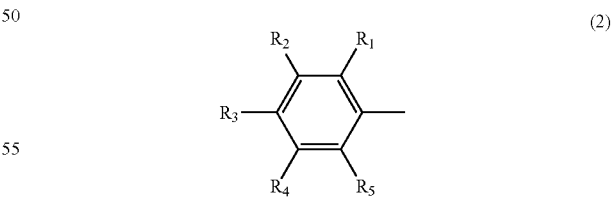

(2)

wherein $R_1$ to $R_5$ are independently a hydrogen atom or a substituent, and at least one of $R_1$ to $R_5$ are a substituted or unsubstituted aryl group having 6 to 30 ring carbon atoms.

6. The organic electroluminescence device according to 5 wherein the substituent represented by the formula (2) is a substituted or unsubstituted 2-biphenyl group.

7. The organic electroluminescence device according to any of 1 to 3 wherein $Ar_1$ and $Ar_2$ are independently a substituted or unsubstituted 1-naphthyl group.

8. The organic electroluminescence device according to any of 1 to 3 wherein $Ar_1$ and $Ar_2$ are independently a substituted or unsubstituted phenanthryl group.
9. The organic electroluminescence device according to any of 1 to 8 wherein the emitting layer further comprises a dopant.
10. The organic electroluminescence device according to 9 wherein the dopant is an aromatic hydrocarbon derivative.
11. The organic electroluminescence device according to 9 wherein the dopant is an amine compound.

According to the invention, it is possible to provide an organic EL device which has high blue color purity and has a long life.

MODE FOR CARRYING OUT THE INVENTION

The organic EL device of the invention is an organic EL device comprising a pair of electrodes and one or more organic compound layers therebetween, the one or more organic compound layers comprising an emitting layer, wherein the emitting layer comprises a pyrene derivative represented by the following formula (1) and the content of the pyrene derivative in the emitting layer is 50 to 100 wt %;

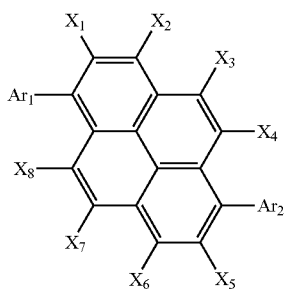

(1)

wherein $Ar_1$ and $Ar_2$ are independently a substituted or unsubstituted aryl group having 6 to 30 ring carbon atoms, $X_1$ to $X_8$ are independently a hydrogen atom, a substituted or unsubstituted aryl group having 6 to 30 ring carbon atoms, a substituted or unsubstituted alkyl group, or a substituted or unsubstituted cycloalkyl group, and at least one of $X_1$ to $X_8$ is a substituted or unsubstituted aryl group having 6 to 30 ring carbon atoms, provided that $Ar_1$ or $Ar_2$ is different from a substituted or unsubstituted aryl group having 6 to 30 ring carbon atoms of $X_1$ to $X_8$. Even If two groups have the same structure, when they bond to the pyrene skeleton at different positions, the two groups are thought to be different groups.

The organic EL device of the invention comprise a pyrene derivative represented by the formula (1) (hereinafter, often simply referred to as the "pyrene derivative of the invention") as a host material. Due to the presence of the pyrene derivative of the invention as a host material, the organic EL device of the invention can have a long life and is capable of emitting blue light having a short wavelength.

In the pyrene derivative of the invention, it is preferred that at least one of $X_1$ to $X_8$ be a substituted or unsubstituted aryl group having 6 to 30 ring carbon atoms, and the remainder of $X_1$ to $X_8$ be all a hydrogen atom. It is more preferred that $X_2$ be a substituted or unsubstituted aryl group having 6 to 30 ring carbon atoms, and $X_1$ and $X_3$ to $X_8$ be a hydrogen atom. Further, it is preferred that $X_2$, $Ar_1$ and $Ar_2$ be not simultaneously the same substituted or unsubstituted aryl group having 6 to 30 ring carbon atoms.

In the pyrene derivative of the invention, it is preferred that $Ar_1$ and $Ar_2$ be the same.

In the pyrene derivative of the invention, it is preferred that $Ar_1$ and $Ar_2$ be independently a substituted or unsubstituted phenyl group.

The substituted or unsubstituted phenyl group is preferably a substituent represented by the following formula (2), with a substituted or unsubstituted 2-biphenyl group being more preferable.

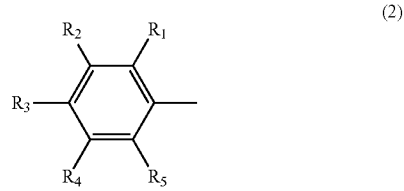

(2)

wherein $R_1$ to $R_5$ are independently a hydrogen atom or a substituent, and at least one of $R_1$ to $R_5$ are a substituted or unsubstituted aryl group having 6 to 30 ring carbon atoms.

In the pyrene derivative of the invention, it is preferred that $Ar_1$ and $Ar_2$ be independently a substituted or unsubstituted 2-biphenyl group, a substituted or unsubstituted 1-naphthyl group or a substituted or unsubstituted phenanthryl group.

If $Ar_1$ and $Ar_2$ are independently a substituted or unsubstituted 2-biphenyl group, a substituted or unsubstituted 1-naphthyl group or a substituted or unsubstituted phenanthryl group, an association of hosts or interaction between a host and a dopant becomes more unlikely to occur due to a large steric hindrance, thereby contributing to improvement in chromaticity of an organic EL device. It is further preferred that $Ar_1$ and $Ar_2$ be a substituted or unsubstituted 1-phenanthryl group, a substituted or unsubstituted 4-phenanthryl group or a substituted or unsubstituted 9-phenanthryl group.

If an association of host molecules is formed in the emitting layer, chromaticity changes.

A pyrene material has a molecule which has a high degree of planarity and tends to form an association easily. By introducing into this pyrene skeleton the above-mentioned substituent which has an effect of increasing steric hindrance and decreasing planarity, it is possible to suppress formation of an association, as well as to improve chromaticity. Further, by decreasing planarity of a host molecule, interaction between a host and a dopant is decreased, thereby contributing to improvement in chromaticity.

Hereinbelow, each substituent of the pyrene derivative of the invention will be explained.

In the invention, the "ring carbon atom" means a carbon atom that forms a saturated ring, an unsaturated ring or an aromatic ring. In the invention, the "aryl group" means a "group which is obtained by removing a hydrogen atom from an aromatic compound", and includes not only a monovalent aryl group but also an "arylene group" which is a divalent group.

The hydrogen atom of the compound of the invention includes light hydrogen and heavy hydrogen.

Examples of the substituted or unsubstituted aryl group having 6 to 30 ring carbon atoms represented by $Ar_1$, $Ar_2$ and $X_1$ to $X_8$ include a substituted or unsubstituted phenyl group, a substituted or unsubstituted naphthyl group, a substituted or unsubstituted phenanthryl group, a substituted or unsubstituted biphenyl group, a substituted or unsubstituted terphenyl group, a substituted or unsubstituted anthryl group, a substituted or unsubstituted chrysenyl group, a substituted or unsubstituted benzophenanthryl group, a substituted or unsubstituted benzanthryl group, a substituted or unsubstituted benzochrysenyl group, a substituted or unsubstituted fluorenyl group, a substituted or unsubstituted 9,9-dimethylfluorenyl group, a substituted or unsubstituted fluoranthenyl group, a substituted or unsubstituted naphtacenyl group and a substituted or unsubstituted triphenylenyl group. Of these, a substituted or unsubstituted phenyl group, a substituted or unsubstituted 1-naphthyl group, a substituted or unsubstituted 2-naphthyl group, a substituted or unsubstituted 1-phenanthryl group, a substituted or unsubstituted 4-phenanthryl group, a substituted or unsubstituted 9-phenanthryl group, a substituted or unsubstituted 2-biphenyl group, a substituted or unsubstituted 3-biphenyl group, a substituted or unsubstituted 4-biphenyl group, a substituted or unsubstituted terphenyl group, a substituted or unsubstituted 9-anthryl group, a substituted or unsubstituted 2-fluorenyl group, a substituted or unsubstituted 9,9-dimethylfluoren-2-yl group, a substituted or unsubstituted 3-fluoranthenyl group, a substituted or unsubstituted 6-chrysenyl group, a substituted or unsubstituted 4-benz[a]anthryl group, a substituted or unsubstituted 7-benz[a]anthryl group or the like are preferable. The aryl group preferably has 6 to 23 ring carbon atoms, more preferably 6 to 20 ring carbon atoms, with 6 to 10 ring carbon atoms being most preferable.

As the substituted or unsubstituted alkyl group represented by $X_1$ to $X_8$, a substituted or unsubstituted ethyl group, a substituted or unsubstituted methyl group, a substituted or unsubstituted i-propyl group, a substituted or unsubstituted n-propyl group, a substituted or unsubstituted s-butyl group, a substituted or unsubstituted t-butyl group, a substituted or unsubstituted pentyl group, a substituted or unsubstituted hexyl group or the like can be given. Of these, a substituted or unsubstituted methyl group, a substituted or unsubstituted i-propyl group, a substituted or unsubstituted t-butyl group and the like are preferable. The alkyl group preferably has 1 to 10 carbon atoms, with 1 to 6 carbon atoms being more preferable.

As the substituted or unsubstituted cycloalkyl group represented by $X_1$ to $X_8$, a substituted or unsubstituted cyclopropyl group, a substituted or unsubstituted cyclobutyl group, a substituted or unsubstituted cyclopentyl group, a substituted or unsubstituted cyclohexyl group, a substituted or unsubstituted 4-methylcyclohexyl group, a substituted or unsubstituted 1-adamantyl group, a substituted or unsubstituted 2-adamantyl group, a substituted or unsubstituted 1-norbornyl group, a substituted or unsubstituted 2-norbornyl group or the like can be given. Of these, a substituted or unsubstituted cyclopentyl group and a substituted or unsubstituted cyclohexyl group are preferable. The cycloalkyl group preferably has 3 to 10 carbon atoms, with 5 to 8 carbon atoms being more preferable.

As the further substituent of each of the substituents of $Ar_1$, $Ar_2$ and $X_1$ to $X_8$, as well as the substituent of $R_1$ to $R_5$, an alkyl group, a cycloalkyl group, an aryl group, an alkenyl group, a silyl group, a cyano group, or the like can be mentioned, for example.

The "further substituent of each of the substituents" means a substituent of an aryl group when the "substituted or unsubstituted aryl group" is a substituted aryl group, for example.

The specific examples of the alkyl group, the cycloalkyl group and the aryl group are as mentioned above.

As the above-mentioned substituted silyl group, a trimethylsilyl group, a triethylsilyl group, a t-butyldimethylsilyl group, a vinyldimethylsilyl group, an isopropyldimethylsilyl group, a triphenylsilyl group, a triisopropylsilyl group or the like can be mentioned. The substituted silyl group is preferably a trimethylsilyl group, a triethylsilyl group and a t-butyldimethylsilyl group.

Specific examples of the pyrene derivative of the invention will be given below.

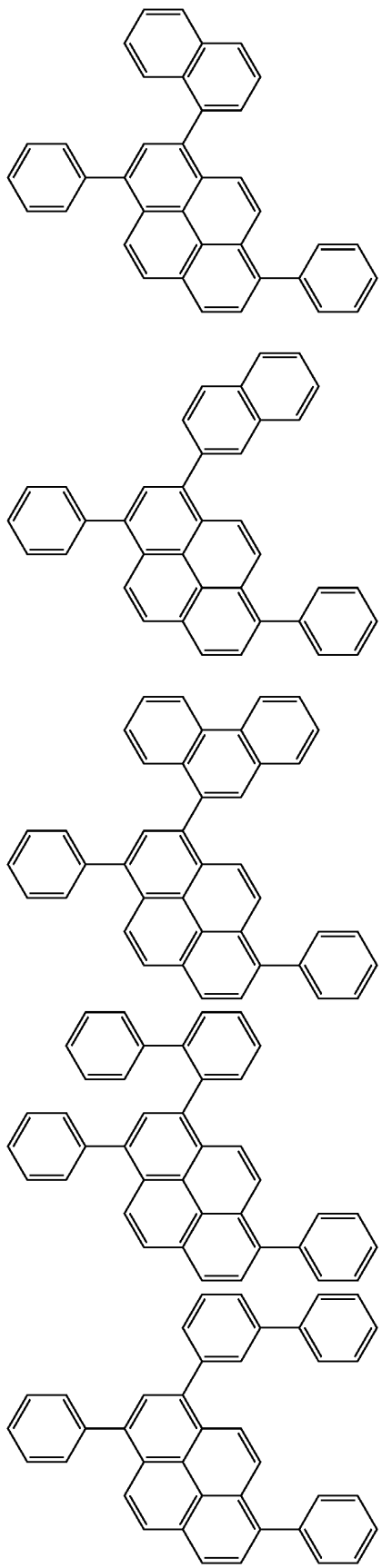

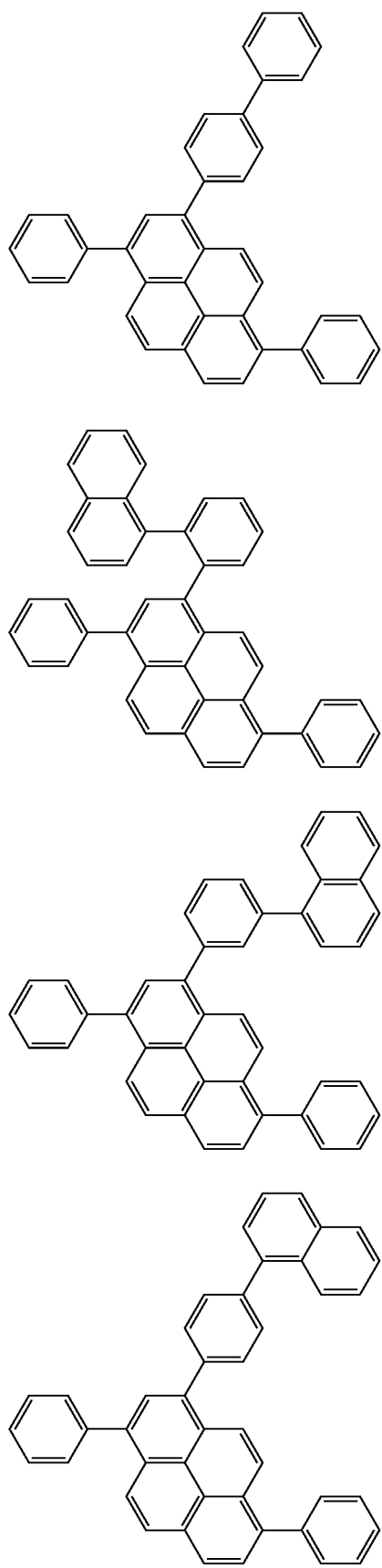
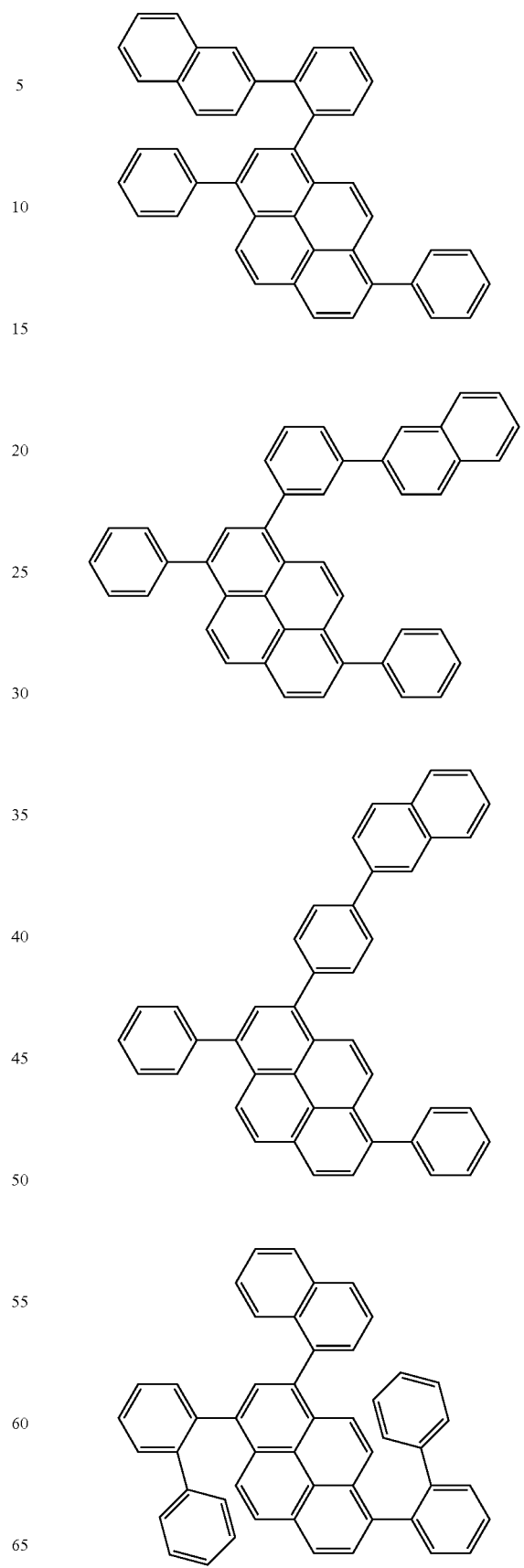

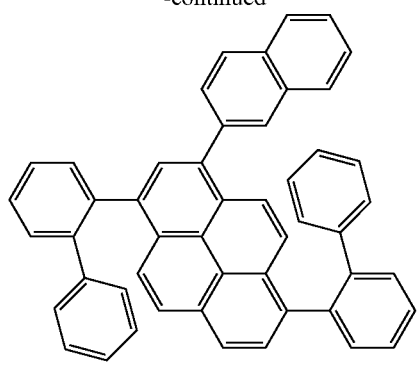
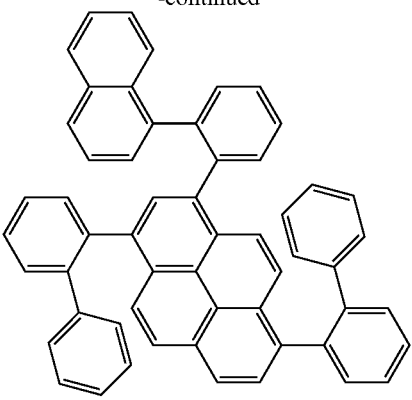
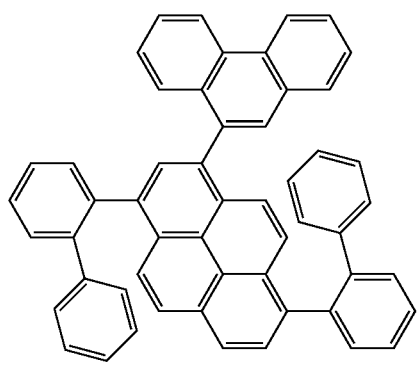
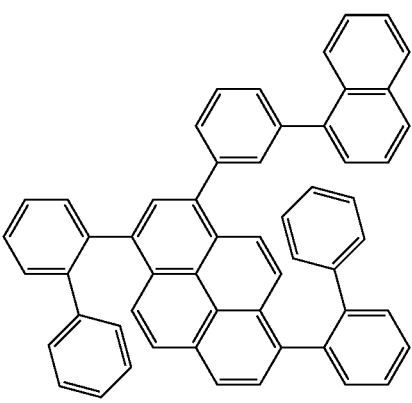
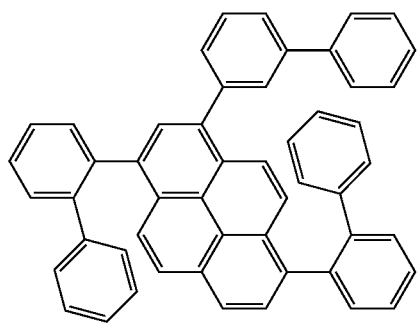
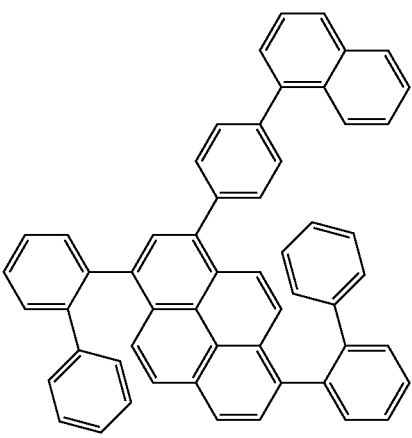
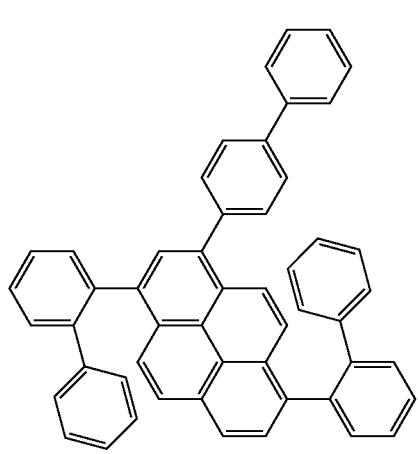
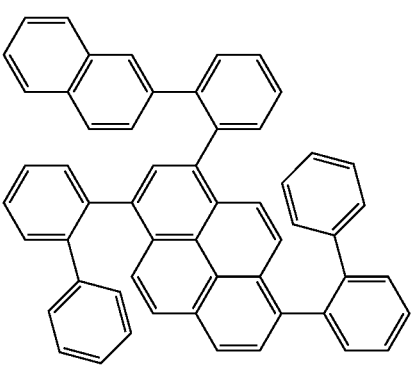

-continued
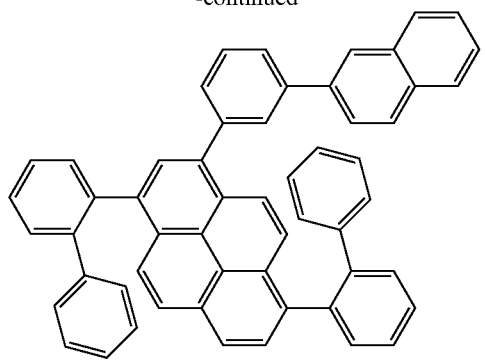
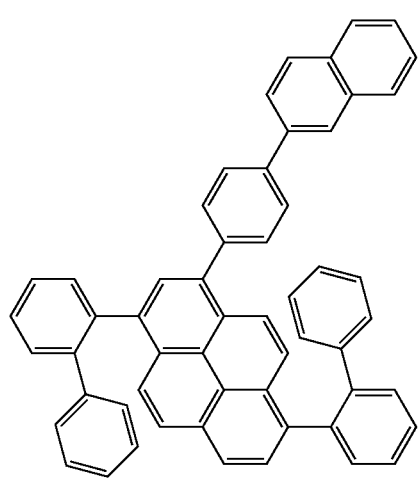
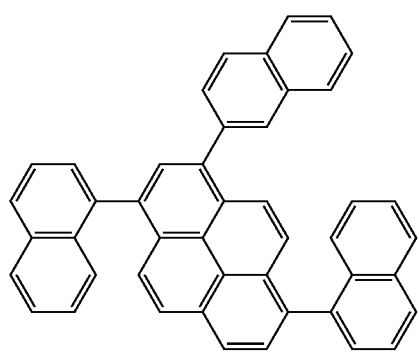
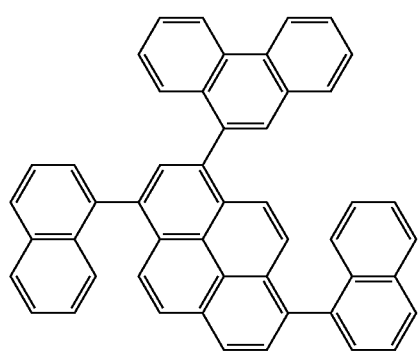
-continued
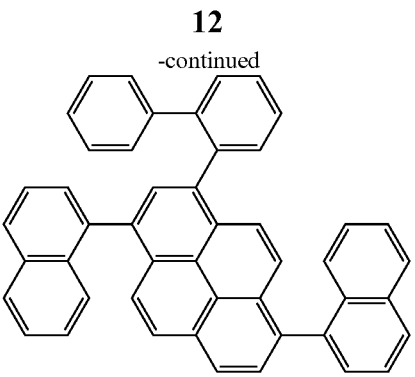
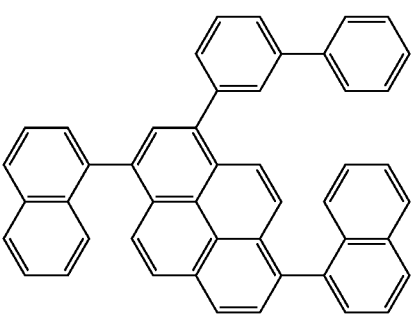
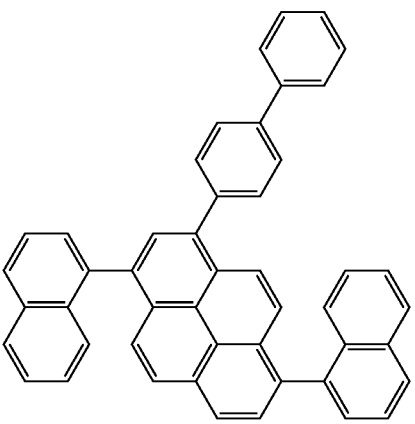
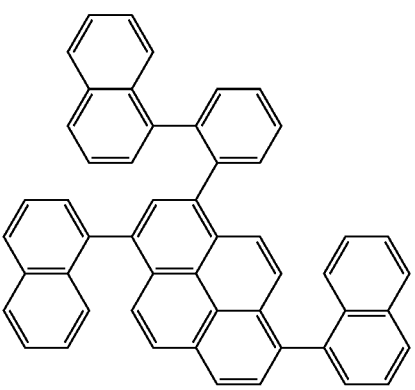

-continued
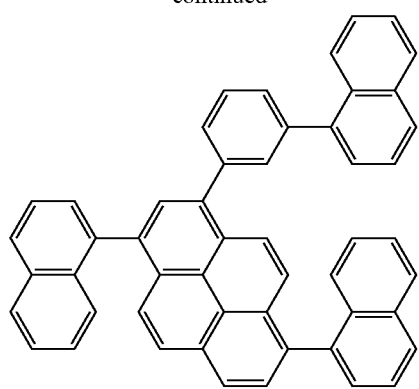
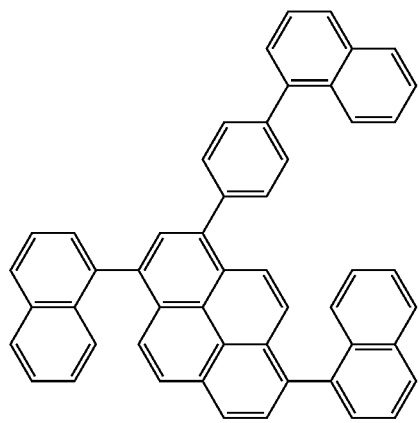
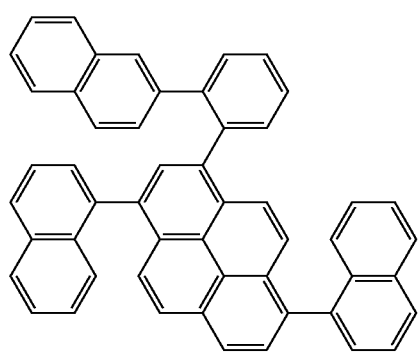
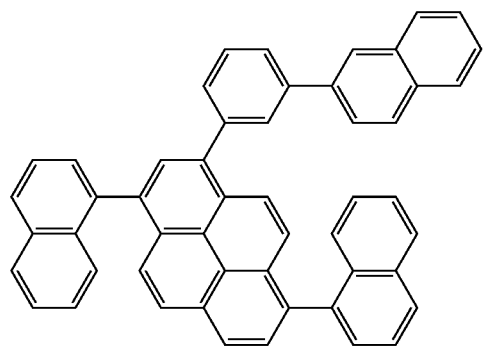
-continued
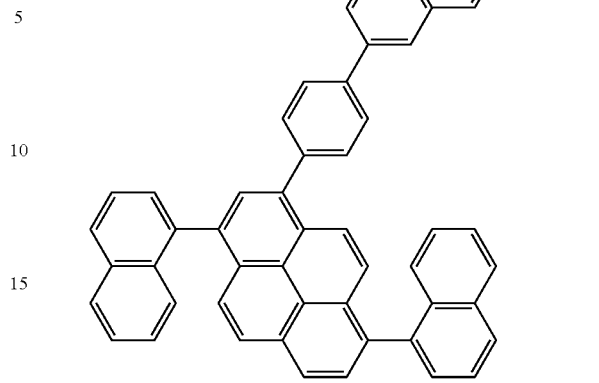
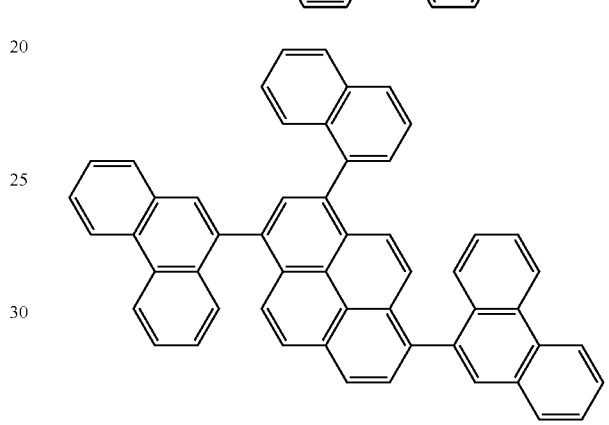
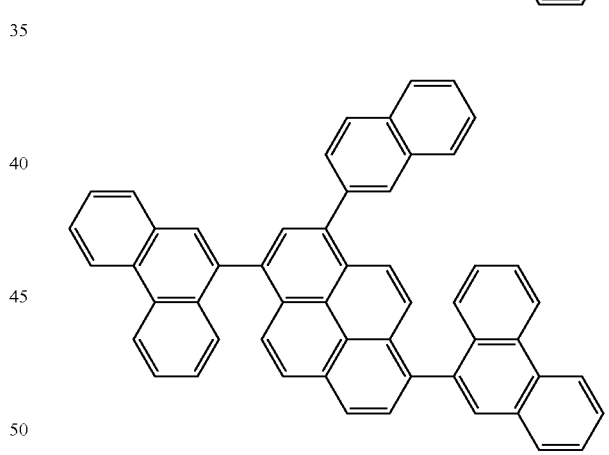
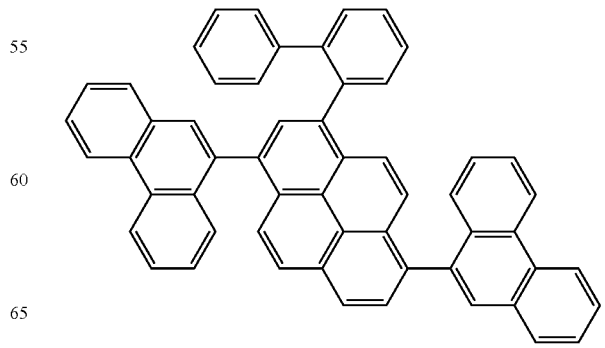

-continued
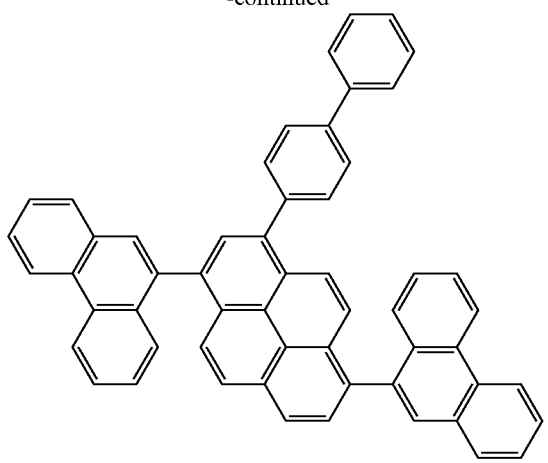
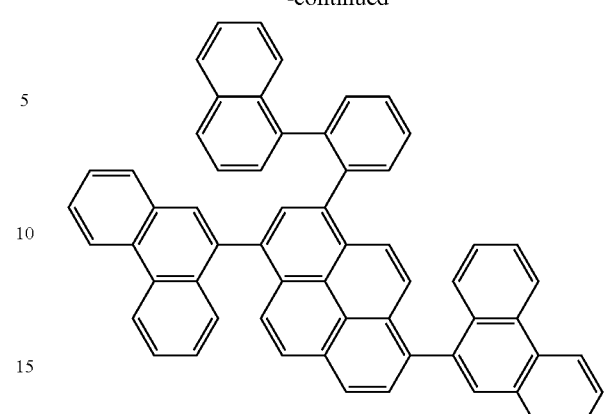
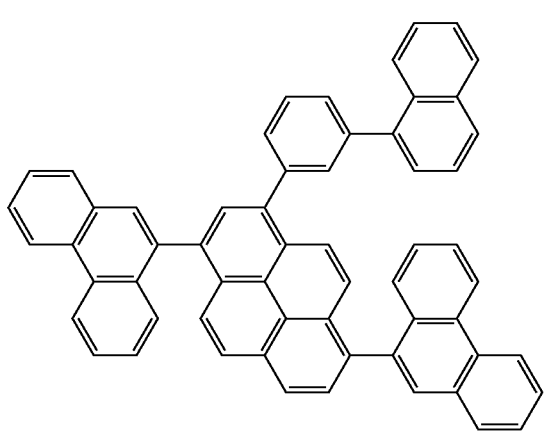
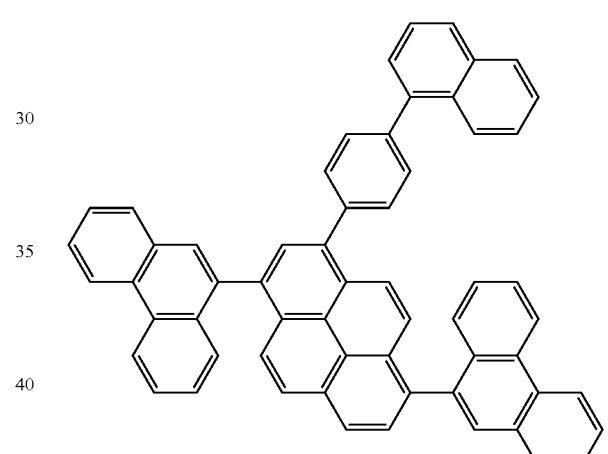
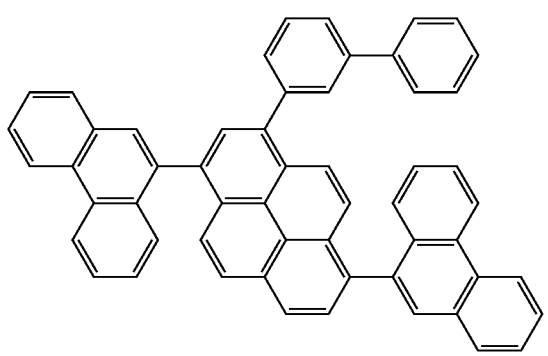
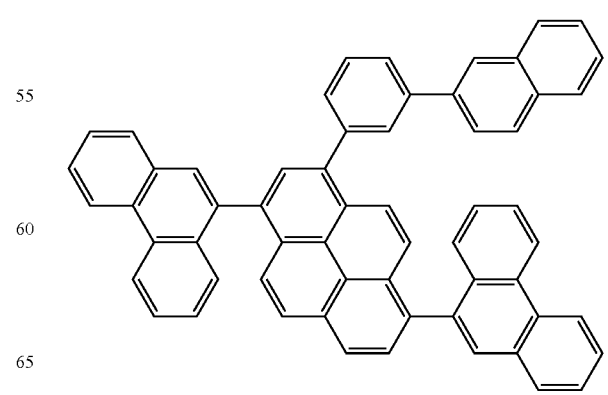

-continued
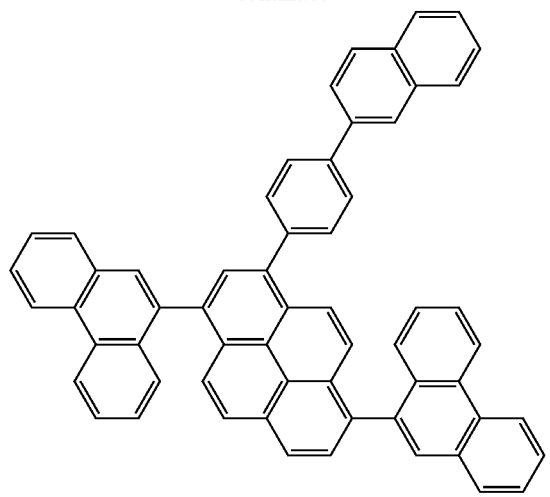
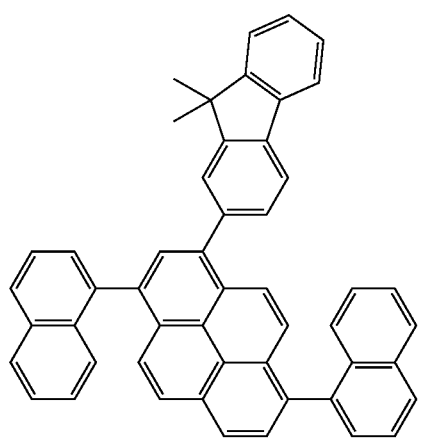
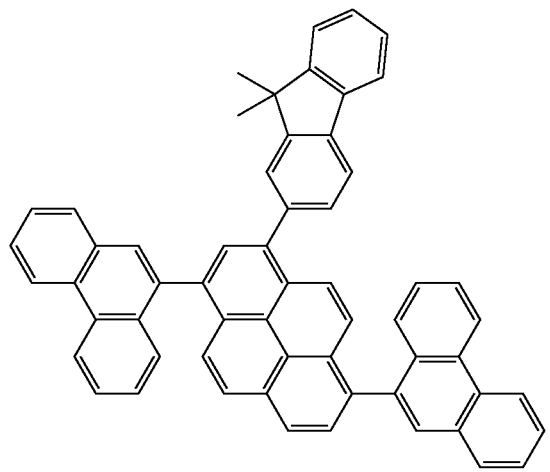
-continued
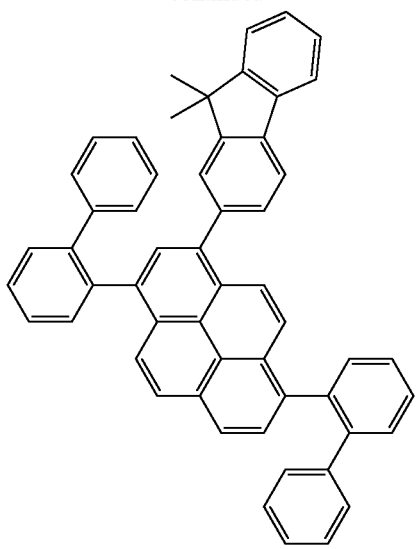
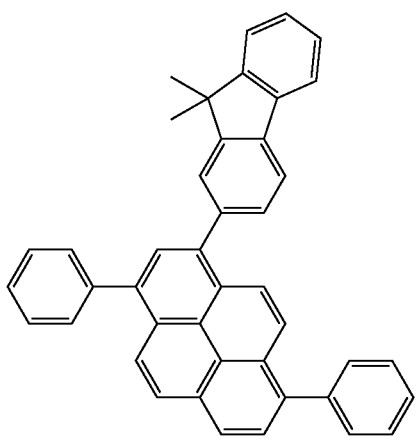
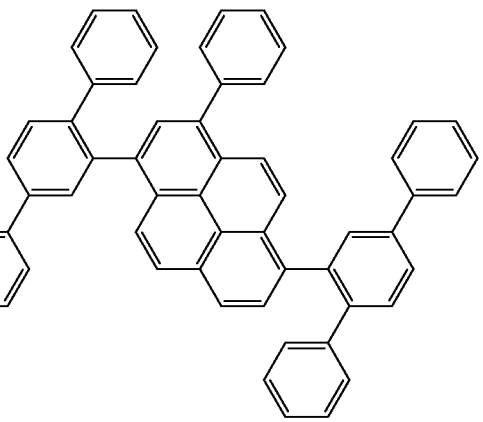

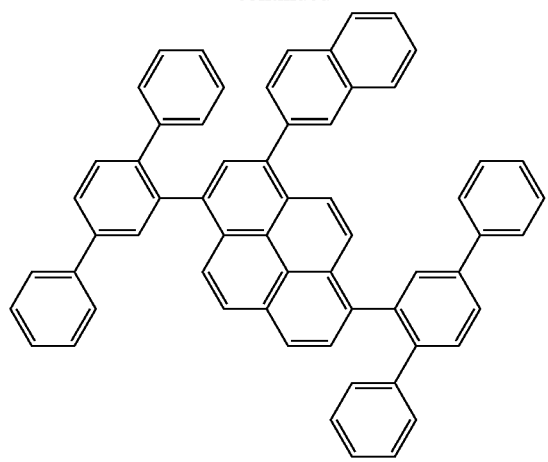
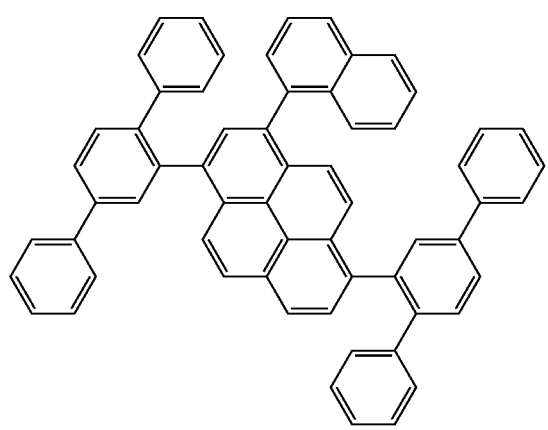
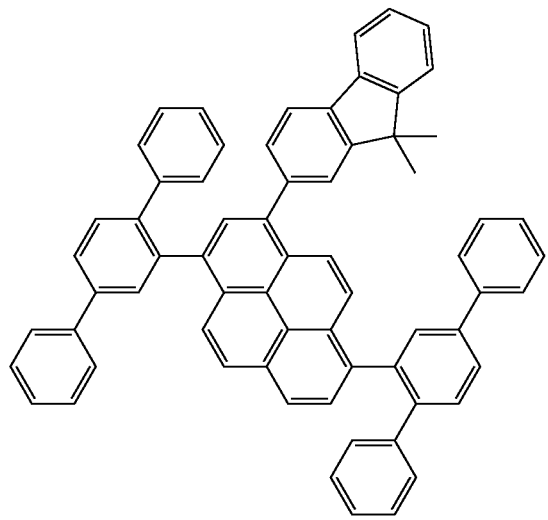
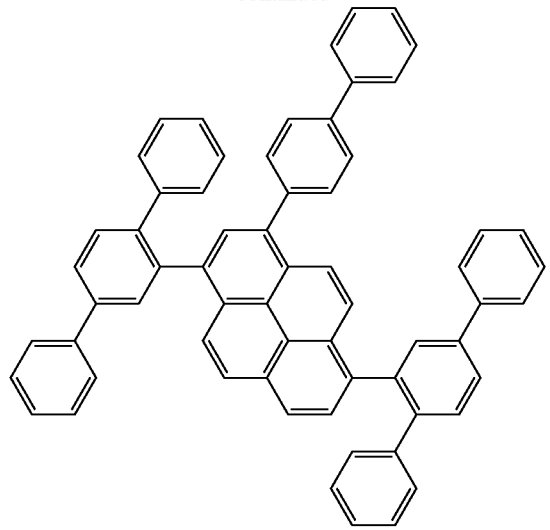
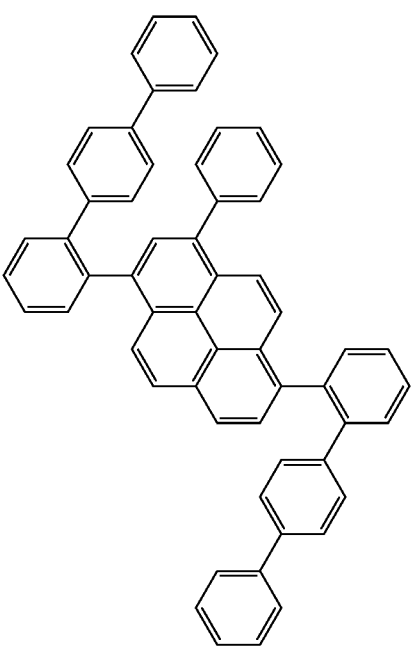

-continued

-continued

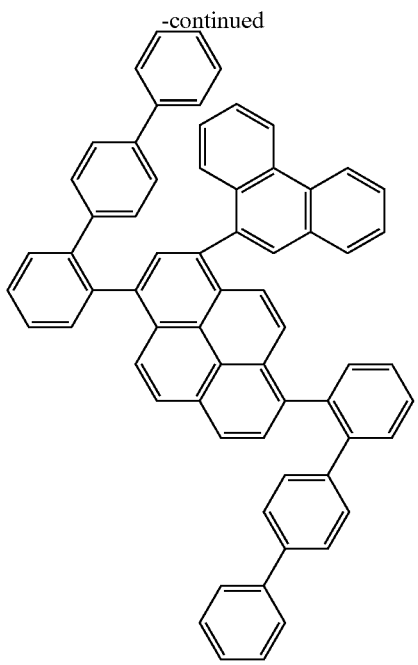

In the organic EL device of the invention, the emitting layer has the following functions:
(1) Injection function: function of allowing injection of holes from the anode or hole-injecting layer and injection of electrons from the cathode or electron-injecting layer upon application of an electric field
(2) Transporting function: function of moving injected carriers (electrons and holes) due to the force of an electric field
(3) Emitting function: function of allowing electrons and holes to recombine therein to emit light As the method for forming the emitting layer, a known method such as deposition, spin coating, or an LB method may be applied. It is preferable that the emitting layer be a molecular deposition film. Here, the molecular deposition film means a thin film formed by deposition of a material compound in a vapor phase or a film formed by solidification of a material compound which is in a solution state or in a liquid state. The molecular deposition film is distinguished from a thin film (molecular accumulation film) formed using the LB method by the difference in aggregation structure or higher order structure or the difference in function due to the difference in structure.

The emitting layer may also be formed by dissolving a binder such as a resin and a material compound in a solvent to obtain a solution, and forming a thin film from the solution by spin coating or the like, as disclosed in JP-A-57-51781.

In the organic EL device of the invention, it is preferred that the emitting layer further comprise, in addition to the pyrene derivative of the invention, a dopant (a phosphorescent dopant and/or a fluorescent dopant). An emitting layer containing other such dopant may be stacked on the emitting layer containing the pyrene derivative of the invention.

A phosphorescent dopant is a compound which can emit light from a triplet exciton. Although the type of the dopant is not particularly restricted as long as it can emit from a triplet exciton, the dopant is preferably a metal complex containing at least one metal selected from the group consisting of Ir, Ru, Pd, Pt, Os and Re. A porphyrine metal complex or an orthometalated metal complex is preferable. A phosphorescent compound may be used singly or in combination of two or more.

As the porphyrin metal complex, a platinum porphyrin complex is preferable.

Various ligands can be given as a ligand for forming an orthometalated metal complex. As preferable ligands, a compound having a phenylpyridine skeleton, a bipyridyl skeleton or a phenanthroline skeleton, or a 2-phenylpyridine derivative, a 7,8-benzoquinoline derivative, a 2-(2-thienyl)pyridine derivative, a 2-(1-naphthyl)pyridine derivative, a 2-phenylquinoline derivative or the like can be given. These ligands may have a substituent, if necessary. In particular, one obtained by introducing a fluoride or a trifluoromethyl group is preferable as a blue dopant. Further, as an auxiliary ligand, the complex may have a ligand other than those mentioned above such as acetyl acetonate and picric acid.

Specific examples of the metal complex include tris(2-phenylpyridine)iridium, tris(2-phenylpyridine)ruthenium, tris(2-phenylpyridine)palladium, bis(2-phenylpyridine)platinum, tris(2-phenylpyridine)osmium, tris(2-phenylpyridine)rhenium, octaethylplatinum porphyrin, octaphenylplatinum porphyrin, octaethylpalladium porphyrin, and octaphenylpalladium porphyrin. However, the metal complex is not limited thereto, and an appropriate complex is selected according to the required emission color, the required device performance and the host compound used.

The content of a phosphorescent dopant in the emitting layer is not particularly restricted, and can be appropriately selected according to the purpose. The content is 0.1 to 50 wt %, for example, with 1 to 30 wt % being preferable. If the content of a phosphorescent compound is less than 0.1 wt %, emission is weak and the effect of the presence of the phosphorescent compound may not be exhibited sufficiently. If the content of a phosphorescent compound exceeds 50 wt %, a phenomenon called concentration quenching may become significant, leading to deterioration of device performance.

A fluorescent dopant is preferably a compound selected from an amine-based compound, an aromatic compound, a chelate derivative such as tris(8-quinolinolato)aluminum complex, a coumarin complex, a tetraphenylbutadiene derivative, a bistyrylarylene derivative and an oxadiazole derivative according to the required emission color. Of these, an amine-based compound and an aromatic compound are preferably used.

An amine-based compound is an aromatic amine derivative having an amino group in its molecule, and examples thereof include a fused polycyclic amine derivative and a styrylamine derivative.

An aromatic compound is an aromatic hydrocarbon derivative having no amino group, and specific examples thereof include an anthracene derivative, a fluorene derivative, a pyrene derivative, a fluoranthene derivative, a benzofluoranthene derivative and a perylene derivative.

As the aromatic amine derivative and the aromatic hydrocarbon derivative, a compound represented by the following formula (10) is preferable.

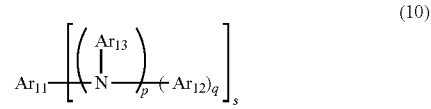
(10)

wherein $Ar_{11}$ is a substituted or unsubstituted anthracene-containing group, a substituted or unsubstituted pyrene-containing group, a substituted or unsubstituted chrysene-containing derivative, a substituted or unsubstituted benzofluoranthene derivative or a substituted or unsubstituted styryl-containing group.

$Ar_{12}$ and $Ar_{13}$ are independently a substituted or unsubstituted aryl group having 6 to 30 ring carbon atoms or a substituted or unsubstituted heterocyclic group having 5 to 30 atoms that form a ring (hereinafter referred to as the "ring atoms").

p and q are independently an integer of 0 or 1 and s is an integer of 1 to 6. If p is 1, q is 1.

The anthracene-containing group is a group having an anthracene skeleton within the molecule.

The pyrene-containing group is a group having a pyrene skeleton within a molecule.

The chrysene-containing group is a group having a chrysene skeleton within the molecule.

The benzofluoranthene-containing group is a group having a benzofluoranthene skeleton within the molecule.

The styryl-containing group is a group having a styryl skeleton-containing derivative within the molecule.

In the invention, the compound (10) is preferably represented by the following formulas (11) to (14):

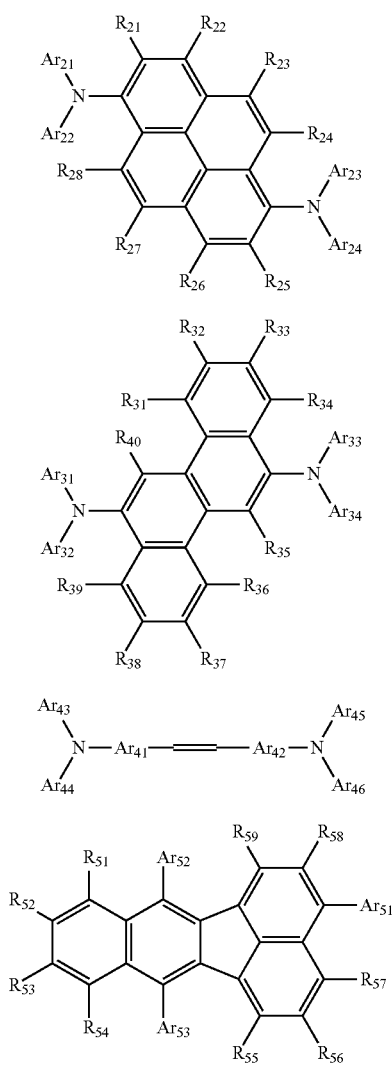

In the formulas, $R_{21}$ to $R_{28}$, $R_{31}$ to $R_{40}$ and $R_{51}$ to $R_{59}$ are independently a hydrogen atom, a fluorine atom, a cyano group, a substituted or unsubstituted alkyl group having 1 to 10 carbon atoms, a substituted or unsubstituted cycloalkyl group having 3 to 10 ring carbon atoms, a substituted or unsubstituted alkylsilyl group having 3 to 30 carbon atoms, a substituted or unsubstituted arylsilyl group having 8 to 30 ring carbon atoms, a substituted or unsubstituted alkoxy group having 1 to 20 carbon atoms, a substituted or unsubstituted aryloxy group having 6 to 20 ring carbon atoms, a substituted or unsubstituted aryl group having 6 to 30 ring carbon atoms or a substituted or unsubstituted heterocyclic group having 5 to 30 ring atoms.

$Ar_{21}$ to $Ar_{24}$, $Ar_{31}$ to $Ar_{34}$, $Ar_{41}$ to $Ar_{46}$ and $Ar_{51}$, to $Ar_{53}$ are independently a substituted or unsubstituted aryl group having 6 to 30 ring carbon atoms or a substituted or unsubstituted heterocyclic group having 5 to 30 ring atoms.

The substituted or unsubstituted aryl group having 6 to 30 ring carbon atoms and the substituted or unsubstituted heterocyclic group having 5 to 30 ring atoms of $Ar_{41}$ and $Ar_{42}$ are independently a corresponding divalent residue.

As the further substituent of each substituent represented by the above formulas (10) to (14), an alkyl group, a cycloalkyl group a substituted or unsubstituted aryl group, a substituted or unsubstituted silyl group, a cyano group or the like can be given.

Meanwhile, the "further substituent of each of the substituents" means a substituent of an aryl group when the "substituted or unsubstituted aryl group" is a substituted aryl group, for example.

The specific examples of each group and each substituent represented by the formulas (11) to (14) will be given below.

As the alkyl group, a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group or the like can be given.

The number of carbon atoms is preferably 1 to 10, more preferably 1 to 8, with 1 to 6 being further preferable. Of these, a methyl group, an ethyl group, a propyl group, an isopropyl group, an n-butyl group, an s-butyl group, an isobutyl group, a t-butyl group, an n-pentyl group and an n-hexyl group are preferable.

As the cycloalkyl group, a cyclopropyl group, a cyclobutyl group, a cyclopentyl group, a cyclohexyl group, a 4-methylcyclohexyl group, a 1-adamantyl group, a 2-adamantyl group, a 1-norbornyl group, a 2-norbornyl group or the like can be given. The number of ring carbon atoms is preferably 3 to 10, more preferably 3 to 8, with 3 to 6 being further preferable.

The alkylsilyl group is represented by —$SiY_3$. Examples of Y are the same as those for the alkyl group. For example, a trimethylsilyl group, a triethylsilyl group, a t-butyldimethylsilyl group, a vinyldimethylsilyl group, a propyldimethylsilyl group or the like can be given.

The arylsilyl group is represented by —$SiZ_3$. Examples of Z are the same as those for the aryl group. For example, a triphenylsilyl group, a phenyldimethylsilyl group, a t-butyldiphenylsilyl group, a tritolylsilyl group, a trixylylsilyl group or the like can be given.

The alkoxy group is represented by —OY. Examples of Y are the same as those for the alkyl group or the aryl group. For example, a methoxy group, an ethoxy group, a butoxy group or the like can be given.

The aryloxy group is represented by —OZ. Examples of Z are the same as those for the aryl group. For example, a phenoxy group can be given.

Examples of the aryl group include a phenyl group, a naphthyl group, an anthryl group, a phenanthryl group, a naphthacenyl group, a pyrenyl group, a chrysenyl group, a benzo[c]phenanthryl group, a benzo[g]chrysenyl group, a triphenylenyl group, a fluorenyl group, a 9,9-dimethylfluorenyl group, a benzofluorenyl group, a dibenzofluorenyl group, a biphenylyl group, a terphenylyl group or the like can be given.

The number of the ring carbon atoms of the aryl group is preferably 6 to 20, more preferably 6 to 14, with 6 to 10 being further preferable. A phenyl group and a naphthyl group are preferable.

Examples of the heterocyclic group include a pyrrolyl group, a pyrazinyl group, a pyridinyl group, an indolyl group, an isoindolyl group, a furyl group, a benzofuranyl group, an isobenzofuranyl group, a dibenzofuranyl group, a dibenzothiophenyl group, a quinolyl group, an isoquinolyl group, a quinoxalinyl group, a carbazolyl group, a phenanthrydinyl group, an acrydinyl group, a phenanthronyl group, a phenazinyl group, a phenothiazinyl group, a phenoxadinyl group, an oxazolyl group, an oxadiazolyl group, a furazanyl group, a thienyl group, a 2-methylpyrrolyl group, a 3-methylpyrrolyl group, a 2-t-butylpyrrolyl group and a 3-(2-phenylpropyl) pyrrolyl group.

The number of the ring carbon atoms of the heterocyclic group is preferably 5 to 20, with 5 to 14 being further preferable. The heterocyclic group is preferably a dibenzofuranyl group, a dibenzothiophenyl group and a carbazolyl group.

The pyrene derivative of the invention can be used not only in the emitting layer but also in the hole-injecting layer, the hole-transporting layer, the electron-injecting layer and the electron-transporting layer.

In the invention, as the organic EL device in which the organic compound layer (organic thin film layer) is composed of plural layers, one in which layers are sequentially stacked (anode/hole-injecting layer/emitting layer/cathode), (anode/emitting layer/electron-injecting layer/cathode), (anode/hole-injecting layer/emitting layer/electron-injecting layer/cathode), (anode/hole-injecting layer/hole-transporting layer/emitting layer/electron-injecting layer/cathode) or the like can be given.

By allowing the organic thin film layer to be composed of plural layers, the organic EL device can be prevented from lowering of luminance or lifetime due to quenching. If necessary, an emitting material, a doping material, a hole-injecting material or an electron-injecting material can be used in combination. Further, due to the use of a doping material, luminance or luminous efficiency may be improved. The hole-injecting layer, the emitting layer and the electron-injecting layer may respectively be formed of two or more layers. In such a case, in the hole-injecting layer, a layer which injects holes from an electrode is referred to as a hole-injecting layer, and a layer which receives holes from the hole-injecting layer and transports the holes to the emitting layer is referred to as a hole-transporting layer. Similarly, in the electron-injecting layer, a layer which injects electrons from an electrode is referred to as an electron-injecting layer and a layer which receives electrons from an electron-injecting layer and transports the electrons to the emitting layer is referred to as an electron-transporting layer. Each of these layers is selected and used according to each of the factors of a material, i.e. the energy level, heat resistance, adhesiveness to the organic layer or the metal electrode or the like.

Examples of the material which can be used in the emitting layer together with the pyrene derivative of the invention include, though not limited thereto, fused polycyclic aromatic compounds such as naphthalene, phenanthrene, rubrene, anthracene, tetracene, pyrene, perylene, chrysene, decacyclene, coronene, tetraphenylcyclopentadiene, pentaphenylcyclopentadiene, fluorene and spirofluorene and derivatives thereof, organic metal complexes such as tris(8-quinolinolate)aluminum, triarylamine derivatives, styrylamine derivatives, stilbene derivatives, coumarin derivatives, pyrane derivatives, oxazone derivatives, benzothiazole derivatives, benzoxazole derivatives, benzimidazole derivatives, pyrazine derivatives, cinnamate derivatives, diketo-pyrrolo-pyrrole derivatives, acrylidone derivatives and quinacridone derivatives.

As the hole-injecting material, a compound which can transport holes, exhibits hole-injecting effects from the anode and excellent hole-injection effect for the emitting layer or the emitting material, and has an excellent capability of forming a thin film is preferable. Specific examples thereof include, though not limited thereto, phthalocyanine derivatives, naphthalocyanine derivatives, porphyline derivatives, benzidine-type triphenylamine, diamine-type triphenylamine, hexacyanohexaazatriphenylene, derivatives thereof, and polymer materials such as polyvinylcarbazole, polysilane and conductive polymers.

Of the hole-injecting materials usable in the organic EL device of the invention, further effective hole-injecting materials are phthalocyanine derivatives.

Examples of the phthalocyanine (Pc) derivative include, though not limited thereto, phthalocyanine derivatives such as $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc and GaPc-O—GaPc, and naphthalocyanine derivatives.

In addition, it is also possible to sensitize carriers by adding to the hole-injecting material an electron-accepting substance such as a TCNQ derivative.

Preferable hole-transporting materials usable in the organic EL device of the invention are aromatic tertiary amine derivatives.

Examples of the aromatic tertiary amine derivative include, though not limited thereto, N,N'-diphenyl-N,N'-dinaphthyl-1,1'-biphenyl-4,4'-diamine, N,N,N',N'-tetrabiphenyl-1,1'-biphenyl-4,4'-diamine or an oligomer or a polymer having these aromatic tertiary amine skeletons.

As the electron-injecting material, a compound which can transport electrons, exhibits electron-injecting effects from the cathode and excellent electron-injection effect for the emitting layer or the emitting material, and has an excellent capability of forming a thin film is preferable.

In the organic EL device of the invention, further effective electron-injecting materials are a metal complex compound and a nitrogen-containing heterocyclic derivative.

Examples of the metal complex compound include, though not limited thereto, 8-hydroxyquinolinate lithium, bis(8-hydroxyquinolinate)zinc, tris(8-hydroxyquinolinate)aluminum, tris(8-hydroxyquinolinate)gallium, bis(10-hydroxybenzo[h]quinolinate)beryllium and bis(10-hydroxybenzo[h]quinolinate)zinc.

As examples of the nitrogen-containing heterocyclic derivative, oxazole, thiazole, oxadiazole, thiadiazole, triazole, pyridine, pyrimidine, triazine, phenanthroline, benzimidazole, imidazopyridine or the like are preferable, for example. Of these, a benzimidazole derivative, a phenanthroline derivative and an imidazopyridine derivative are preferable.

As a preferred mode, a dopant is further contained in these electron-injecting materials. In order to facilitate receiving electrons from the cathode, it is more preferable to dope the vicinity of the cathode interface of the second organic layer with a dopant, the representative example of which is an alkali metal.

As the dopant, a donating metal, a donating metal compound and a donating metal complex can be given. These reducing dopants may be used singly or in combination of two or more.

In the organic EL device of the invention, the emitting layer may contain, in addition to at least one selected from the pyrene derivatives represented by the formulas (1), at least one of an emitting material, doping material, hole-injecting material, hole-transporting material and electron-injecting material in the same layer. Moreover, for improving stability of the organic EL device obtained by the invention to temperature, humidity, atmosphere, etc. it is also possible to prepare a protective layer on the surface of the device, and it is also possible to protect the entire device by applying silicone oil, resin, etc.

As the conductive material used in the anode of the organic EL device of the invention, a conductive material having a work function of more than 4 eV is suitable. Carbon, aluminum, vanadium, iron, cobalt, nickel, tungsten, silver, gold, platinum, palladium or the like, alloys thereof, oxidized metals which are used in an ITO substrate and a NESA substrate such as tin oxide and indium oxide and organic conductive resins such as polythiophene and polypyrrole are used. As the conductive material used in the cathode, a conductive material having a work function of smaller than 4 eV is suitable. Magnesium, calcium, tin, lead, titanium, yttrium, lithium, ruthenium, manganese, aluminum, and lithium fluoride or the like, and alloys thereof are used, but not limited thereto. Representative examples of the alloys include, though not limited thereto, magnesium/silver alloys, magnesium/indium alloys and lithium/aluminum alloys. The amount ratio of the alloy is controlled by the temperature of the deposition source, atmosphere, vacuum degree or the like, and an appropriate ratio is selected. If necessary, the anode and the cathode each may be composed of two or more layers.

In the organic EL device of the invention, in order to allow it to emit light efficiently, it is preferred that at least one of the surfaces be fully transparent in the emission wavelength region of the device. In addition, it is preferred that the substrate also be transparent. The transparent electrode is set such that predetermined transparency can be ensured by a method such as deposition or sputtering by using the above-mentioned conductive materials. It is preferred that the electrode on the emitting surface have a light transmittance of 10% or more. Although no specific restrictions are imposed on the substrate as long as it has mechanical and thermal strength and transparency, a glass substrate and a transparent resin film can be given.

Each layer of the organic EL device of the invention can be formed by a dry film-forming method such as vacuum vapor deposition, sputtering, plasma ion coating, ion plating or the like or a wet film-forming method such as spin coating, dipping, flow coating or the like. Although the film thickness is not particularly limited, it is required to adjust the film thickness to an appropriate value. If the film thickness is too large, a large voltage is required to be applied in order to obtain a certain optical output, which results in a poor efficiency. If the film thickness is too small, pinholes or the like are generated, and a sufficient luminance cannot be obtained even if an electrical field is applied. The suitable film thickness is normally 5 nm to 10 μm, with a range of 10 nm to 0.2 μm being further preferable.

In the case of the wet film-forming method, a thin film is formed by dissolving or dispersing materials forming each layer in an appropriate solvent such as ethanol, chloroform, tetrahydrofuran and dioxane. Any of the above-mentioned solvents can be used.

As the solvent suited to such a wet film-forming method, a solution containing the pyrene derivative of the invention as an organic EL material and a solvent can be used.

It is preferred that the organic EL material contain a host material and a dopant material, that the host material be the pyrene derivative of the invention, and that the dopant material be at least one selected from the dopants mentioned above.

In each organic thin film layer, an appropriate resin or additive may be used in order to improve film-forming properties, to prevent generation of pinholes in the film, or for other purposes.

The organic EL device of the invention can be suitably used as a planar emitting body such as a flat panel display of a wall-hanging television, backlight of a copier, a printer or a liquid crystal display, light sources for instruments, a display panel, navigation light, or the like. The compound of the invention can be used not only in an organic EL device but also in the field of an electrophotographic photoreceptor, a photoelectric converting element, a solar cell and an image sensor.

EXAMPLES

Production Example 1

Compound 1 was synthesized according to the following scheme.

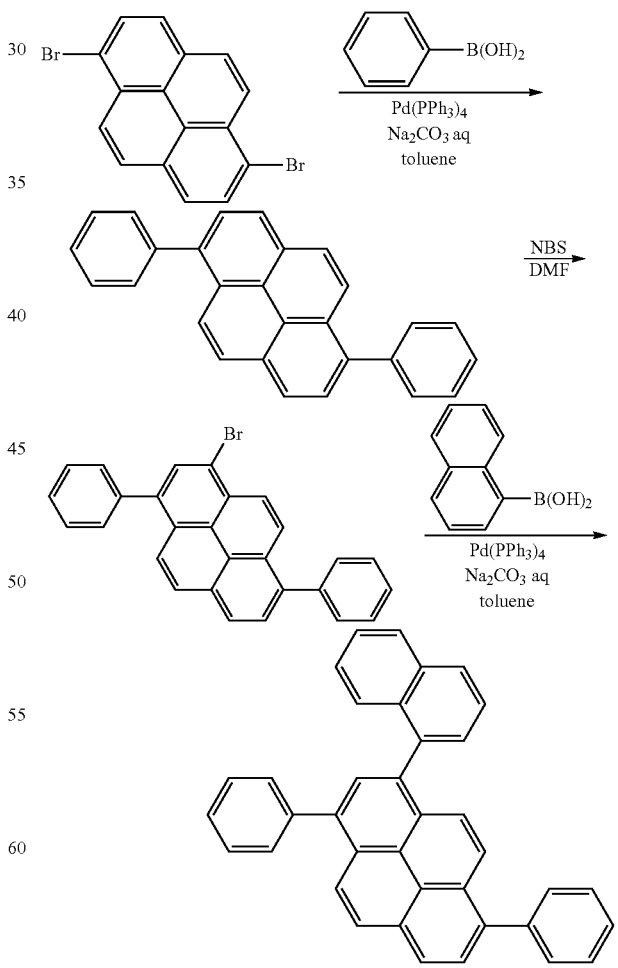

Compound 1

Synthesis of 1,6-diphenylpyrene

Under an argon atmosphere, 15.0 g of 1,6-dibromopyrene, 13.2 g of phenylboronic acid, 1.9 g of tetrakis(triphenylphosphine)palladium (0) [Pd(PPh$_3$)$_4$], 27.8 g of sodium carbonate (130 mL of clean water), toluene and tetrahydrofuran were placed into a flask, and the resulting mixture was allowed to react at 90° C. for 7 hours. After cooling, the reaction solution was filtered, and solids obtained were washed with methanol and clean water. Further, the solids were purified by silica gel chromatography (heated toluene). The resulting crude product which was obtained by a concentration was re-crystallized from toluene, followed by drying under a reduced pressure, whereby white solids of 1,6-diphenylpyrene (11.8 g) were obtained.

Synthesis of 3-bromo-1,6-diphenylpyrene

Under a flow of argon, 11.8 g of 1,6-diphenylpyrene, 5.93 g of N-bromosuccinimide and DMF were placed into a flask. The resulting mixture was allowed to react at 60° C. for 2 days. After cooling, the reaction solution was filtered, and solids obtained were washed with clean water, methanol and clean water, and solids obtained were dried under a reduced pressure, whereby white solids of 3-bromo-1,6-diphenylpyrene (8.60 g) were obtained.

Synthesis of Compound 1

Under an argon atmosphere, 8.60 g of 3-bromo-1,6-diphenylpyrene, 4.13 g of 1-naphthylboronic acid, 0.462 g of tetrakis(triphenylphosphine)palladium (0) [Pd(PPh$_3$)$_4$], 80 mL of toluene and 40 mL of 2M sodium carbonate were placed into a flask, and the resulting mixture was allowed to react at 90° C. for 7 hours. After cooling, the reaction solution was filtered, and solids obtained were washed with methanol and clean water. Further, the solids were purified by silica gel chromatography, whereby 6.73 g of white solids were obtained.

As a result of mass spectrometry, the crystals obtained were identified to be Compound 1, and m/e was 480 for molecular weight of 480.19.

Production Example 2

Compound 2 was synthesized according to the following scheme.

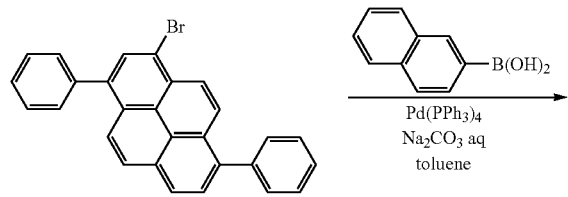

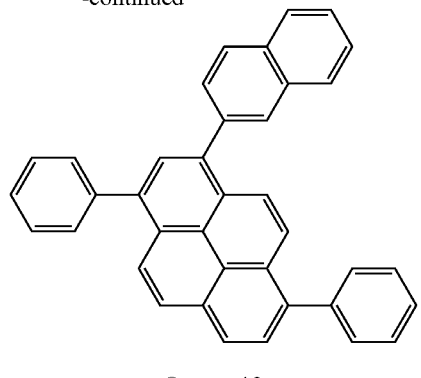

Compound 2

Compound 2 was synthesized by conducting a reaction in the same manner as in Production Example 1, except that 1-naphthylboronic acid was used instead of 2-naphthylboronic acid.

Compound 2 was identified by mass spectroscopy, and m/e was 480 for molecular weight of 480.19.

Production Example 3

Compound 3 was synthesized according to the following scheme.

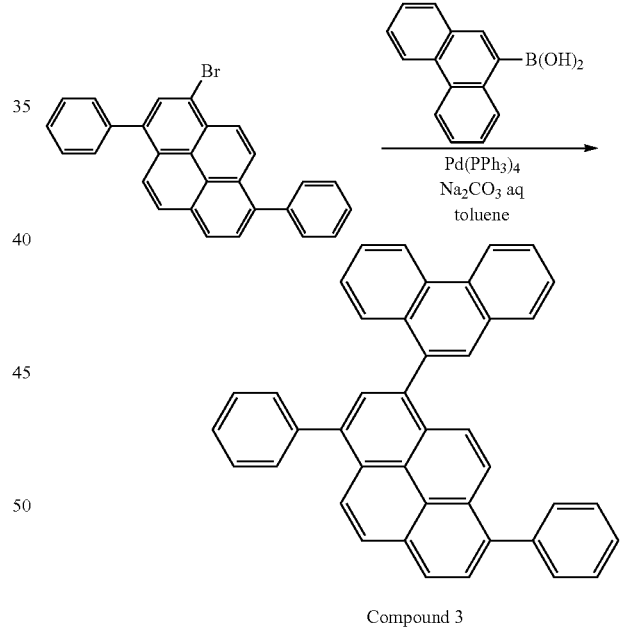

Compound 3

Compound 3 was synthesized by conducting a reaction in the same manner as in Production Example 1, except that 9-phenanthrenylboronic acid was used instead of 1-naphthylboronic acid.

Compound 3 was identified by mass spectroscopy, and m/e was 530 for molecular weight of 530.20.

Production Example 4

Compound 4 was synthesized according to the following scheme.

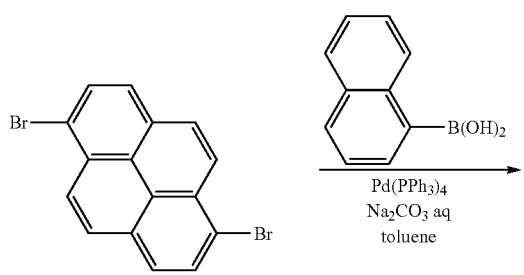

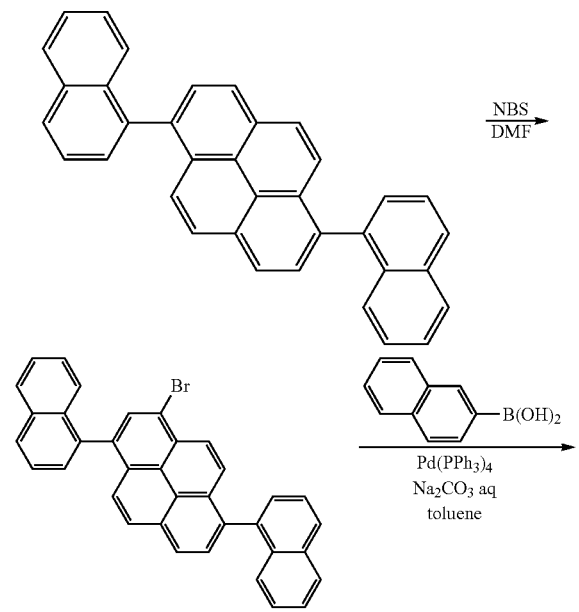

Compound 4

Compound 4 was synthesized by conducting a reaction in the same manner as in Production Example 1, except that 1-naphthylboronic acid was used instead of phenylboronic acid in the synthesis of 1,6-diphenylpyrene and 2-naphthylboronic acid was used instead of 1-naphthylboronic acid.

Compound 4 was identified by mass spectroscopy, and m/e was 580 for molecular weight of 580.22.

Production Example 5

Compound 5 was synthesized according to the following scheme.

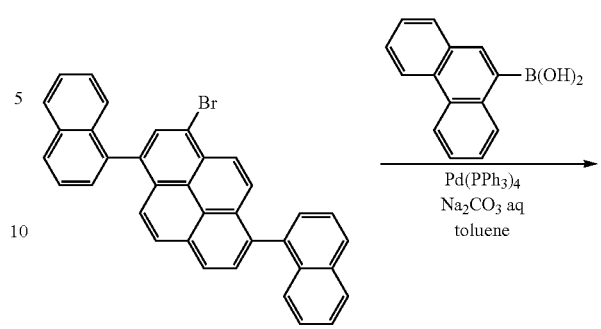

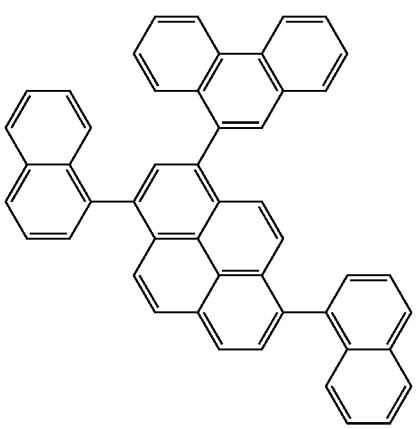

Compoumd 5

Compound 5 was synthesized by conducting a reaction in the same manner as in Production Example 4, except that 9-phenanthrenylboronic acid was used instead of 2-naphthylboronic acid.

Compound 5 was identified by mass spectroscopy, and m/e was 630 for molecular weight of 630.23.

Production Example 6

Compound 6 was synthesized according to the following scheme.

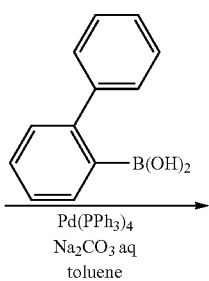

Production Example 7

Compound 7 was synthesized according to the following scheme.

Compound 7

Compound 7 was synthesized by conducting a reaction in the same manner as in Production Example 6, except that 2-naphthylboronic acid was used instead of 1-naphthylboronic acid.

Compound 7 was identified by mass spectroscopy, and m/e was 632 for molecular weight of 632.25.

Production Example 8

Compound 8 was synthesized according to the following scheme.

Compound 6

Compound 6 was synthesized by conducting a reaction in the same manner as in Production Example 1, except that 2-biphenylboronic acid was used instead of phenylboronic acid in the synthesis of 1,6-diphenylpyrene.

Compound 6 was identified by mass spectroscopy, and m/e was 632 for molecular weight of 632.25.

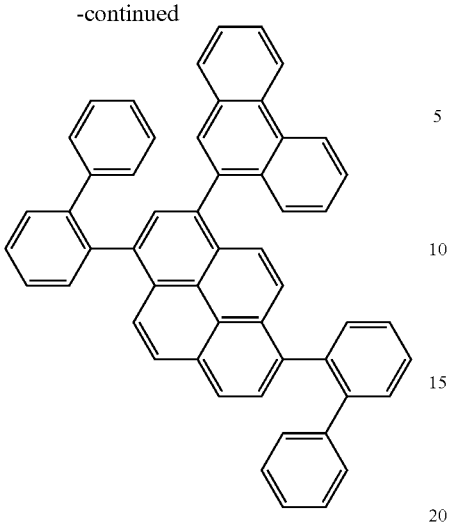

Compound 8

Compound 8 was synthesized by conducting a reaction in the same manner as in Production Example 6, except that 9-phenanthrenylboronic acid was used instead of 1-naphthylboronic acid.

Compound 8 was identified by mass spectroscopy, and m/e was 682 for molecular weight of 682.27.

Production Example 9

Compound 9 was synthesized according to the following scheme.

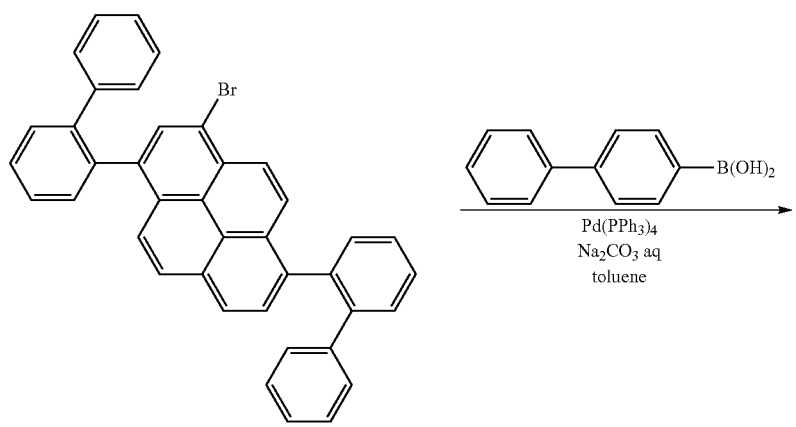

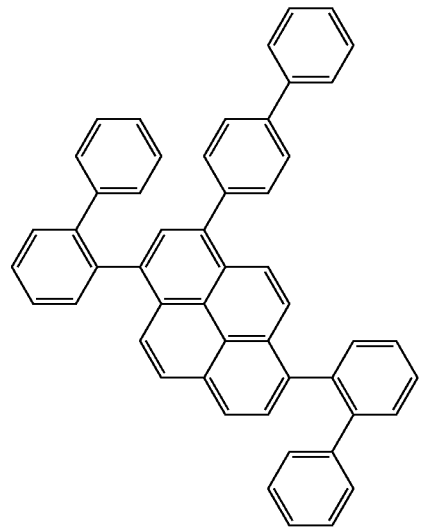

Compound 9

Compound 9 was synthesized by conducting a reaction in the same manner as in Production Example 6, except that 2-biphenylboronic acid was used instead of 1-naphthylboronic acid.

Compound 9 was identified by mass spectroscopy, and m/e was 658 for molecular weight of 658.27.

Production Example 10

Compound 10 was synthesized according to the following scheme.

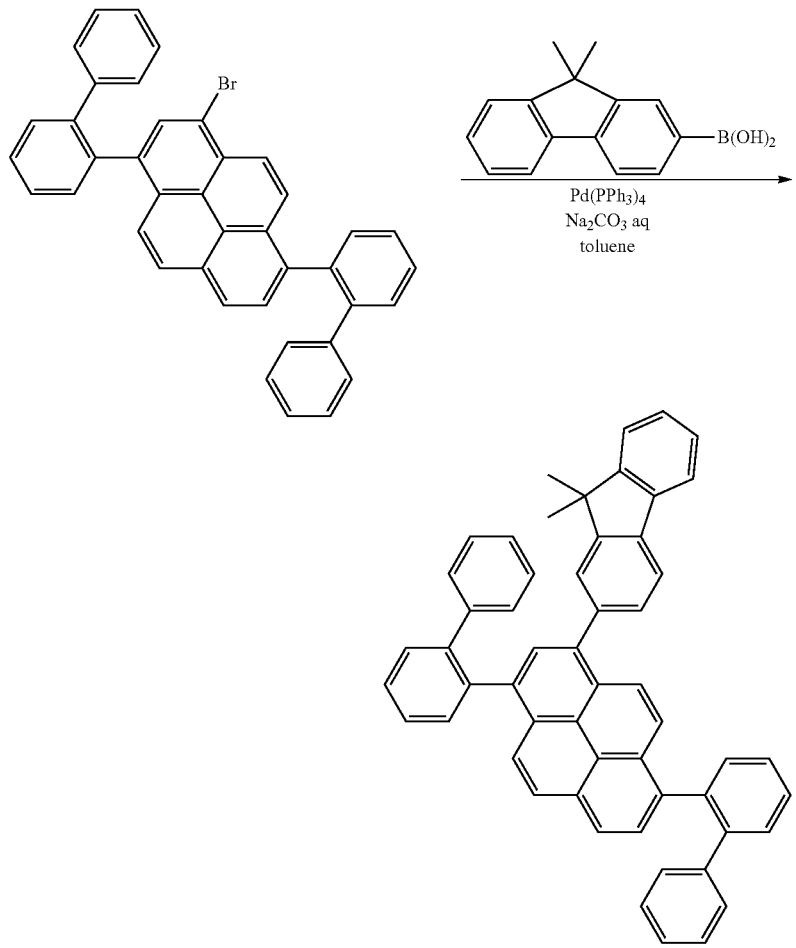

Compound 10

Compound 10 was synthesized by conducting a reaction in the same manner as in Production Example 6, except that 2-(9,9-dimethylfluorenyl)boronic acid was used instead of 1-naphthylboronic acid.

Compound 10 was identified by mass spectroscopy, and m/e was 698 for molecular weight of 698.30.

Production Example 11

Compound 11 was synthesized according to the following scheme.

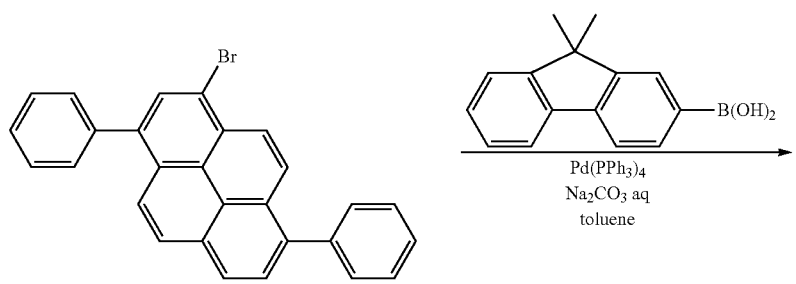

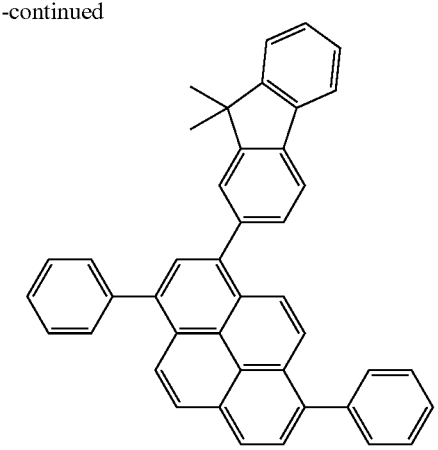

Compound 11

Compound 11 was synthesized by conducting a reaction in the same manner as in Production Example 1, except that 2-(9,9-dimethylfluorenyl)boronic acid was used instead of 1-naphthylboronic acid.

Compound 11 was identified by mass spectroscopy, and m/e was 546 for molecular weight of 546.23.

Example 1

A glass substrate, measuring 25 mm×75 mm×1.1 mm thick, with an ITO transparent electrode (manufactured by Geomatics Co.) was subjected to ultrasonic cleaning in isopropyl alcohol for 5 minutes and then to UV ozone cleaning for 30 minutes. The cleaned glass substrate with transparent electrode lines was mounted on a substrate holder in a vacuum deposition device. First, a 50 nm thick compound A-1 film was formed on the surface where the transparent electrode lines were formed, so as to cover the transparent electrode. The compound A-1 film functioned as a hole-injecting layer. After the formation of the A-1 film, a 45 nm thick compound A-2 film was formed thereon as a hole-transporting layer. On the A-2 film, the compound 1 and compound D-1 were deposited in a film thickness ratio of 20:1 to form a 20 nm thick blue color emitting layer. On the thus formed emitting layer, compound ET-1 was deposited in a thickness of 30 nm as the electron-injecting layer. Subsequently, LiF was deposited in a thickness of 1 nm, followed by deposition of aluminum in a thickness of 150 nm to form a metal cathode, whereby an organic EL device was fabricated.

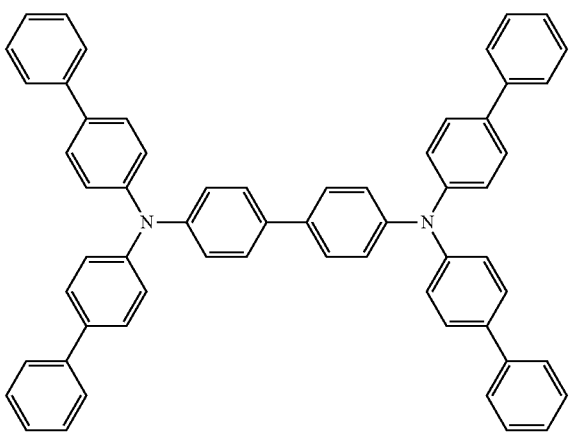

A-2

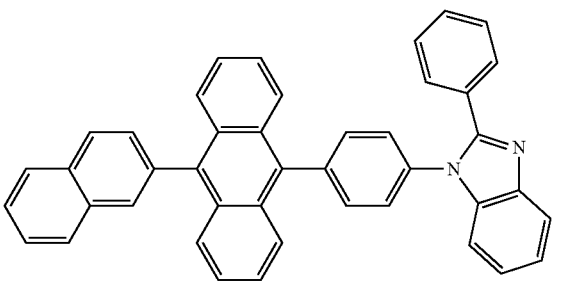

ET-1

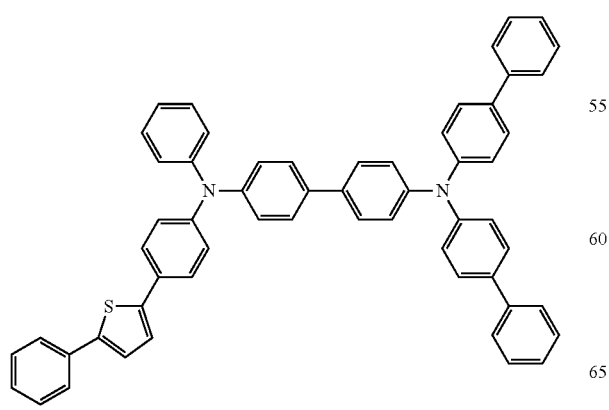

A-1

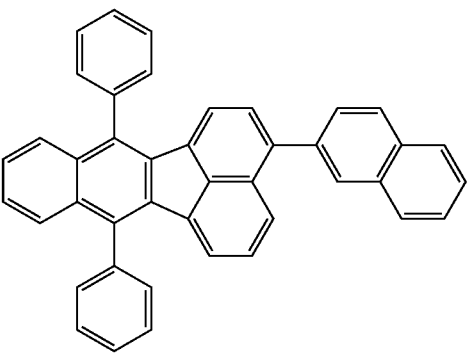

D-1

For the thus fabricated organic EL device, the voltage at the time of driving at a current density of 10 mA/cm², the external quantum yield (EQE), the chromaticity, and a half life at an initial luminance of 500 cd/m² were measured. The methods for the measuring are shown below.

The results are shown in Table 1.

The x and y of chromaticity CIE 1931: measured by a spectroradiometer (CS1000, produced by MINOLTA).

External quantum yield: Current having a current density of 10 mA/cm² was applied to the thus obtained organic EL device. Emission spectra thereof were measured with a spectroradiometer (CS-1000, produced by MINOLTA), and external quantum efficiency was calculated by the following equation (1):

$$E.Q.E. = \frac{N_P}{N_E} \times 100$$

$$= \frac{(\pi/10^9)\int \phi(\lambda)\cdot d\lambda \cdot \frac{hc}{\ }}{\frac{J/10}{e}} \times 100 \quad \text{formula (1)}$$

$$= \frac{(\pi/10^9)\sum(\phi(\lambda)\cdot(\lambda))\cdot \frac{hc}{\ }}{\frac{J/10}{e}} \times 100(\%)$$

$N_P$: Number of photons
$N_E$: Number of electrons
$\pi$: Circular constant=3.1416
$\lambda$: Wavelength (nm)
$\phi$: Luminescence intensity (W/sr·m²·nm)
h: Planck constant=6.63×10⁻³⁴ (J·s)
c: Light velocity=3×10⁸ (m/s)
J: Current density (mA/cm²)
e: Charge=1.6×10⁻¹⁹ (C)

Examples 2 to 11 and Comparative Examples 1 to 4

An organic EL device was fabricated and evaluated in the same manner as in Example 1, except that materials shown in Table 1 are used as a host and a dopant of the emitting layer. The results obtained are shown in Table 1.

TABLE 1

H-1

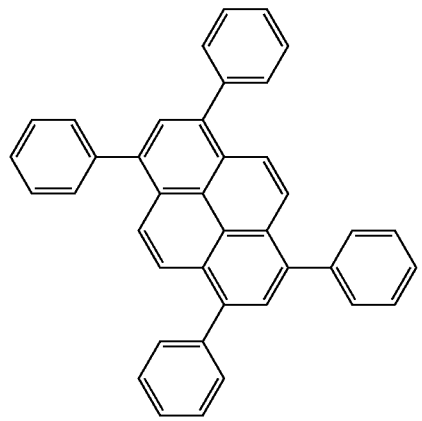 [SMILES: c1ccc(-c2cc(-c3ccccc3)c3ccc4c(-c5ccccc5)cc(-c5ccccc5)c5ccc2c3c54)cc1]

H-2

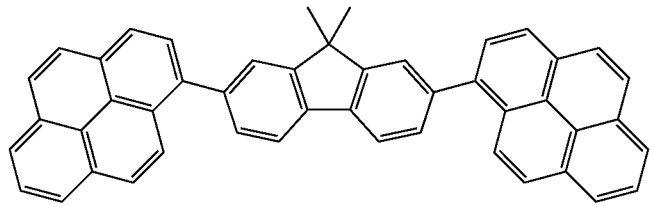 [SMILES: CC1(C)c2cc(-c3ccc4ccc5cccc6ccc3c4c56)ccc2-c2ccc(-c3ccc4ccc5cccc6ccc3c4c56)cc21]

H-3

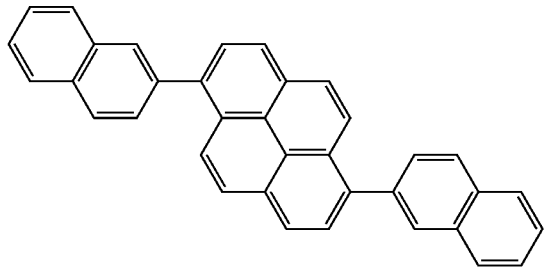 [SMILES: c1ccc2cc(-c3ccc4ccc5c(-c6ccc7ccccc7c6)ccc6ccc3c4c65)ccc2c1]

TABLE 1-continued

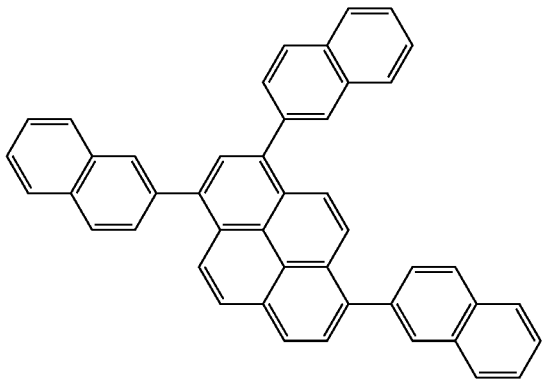 [SMILES: c1ccc2cc(-c3ccc4ccc5c(-c6ccc7ccccc7c6)cc(-c6ccc7ccccc7c6)c6ccc3c4c56)ccc2c1]

H-4

| | Host | Dopant | Voltage (V) | Chromaticity CIEx | CIEy | EQE (%) | Lifetime (h) |
|---|---|---|---|---|---|---|---|
| Example 1 | Compound 1 | D-1 | 3.1 | 0.147 | 0.112 | 5.8 | 5000 |
| Example 2 | Compound 2 | D-1 | 3.1 | 0.147 | 0.116 | 5.7 | 4500 |
| Example 3 | Compound 3 | D-1 | 3.2 | 0.147 | 0.112 | 5.7 | 5500 |
| Example 4 | Compound 4 | D-1 | 3.2 | 0.148 | 0.107 | 5.8 | 4500 |
| Example 5 | Compound 5 | D-1 | 3.2 | 0.148 | 0.105 | 5.6 | 4500 |
| Example 6 | Compound 6 | D-1 | 3.4 | 0.146 | 0.093 | 5.8 | 4800 |
| Example 7 | Compound 7 | D-1 | 3.4 | 0.146 | 0.095 | 5.8 | 4700 |
| Example 8 | Compound 8 | D-1 | 3.4 | 0.146 | 0.096 | 5.9 | 4900 |
| Example 9 | Compound 9 | D-1 | 3.4 | 0.146 | 0.096 | 5.8 | 5000 |
| Example 10 | Compound 10 | D-1 | 3.3 | 0.146 | 0.095 | 5.9 | 4800 |
| Example 11 | Compound 11 | D-1 | 3.1 | 0.147 | 0.112 | 5.7 | 4600 |
| Com. Example 1 | H-1 | D-1 | 3.4 | 0.146 | 0.119 | 4.9 | 1500 |
| Com. Example 2 | H-2 | D-1 | 3.6 | 0.147 | 0.131 | 4.8 | 4000 |
| Com. Example 3 | H-3 | D-1 | 4.4 | 0.147 | 0.132 | 4.7 | 1900 |
| Com. Example 4 | H-4 | D-1 | 3.4 | 0.147 | 0.141 | 4.9 | 4000 |

Example 12

A glass substrate, measuring 25 mm×75 mm×1.1 mm thick, with an ITO transparent electrode (manufactured by Geomatics Co.) was subjected to ultrasonic cleaning in isopropyl alcohol for 5 minutes and then to UV ozone cleaning for 30 minutes. The cleaned glass substrate with transparent electrode lines was mounted on a substrate holder in a vacuum deposition device. First, a 50 nm thick compound A-1 film was formed on the surface where the transparent electrode lines were formed, so as to cover the transparent electrode. The compound A-1 film functioned as a hole-injecting layer. After the formation of the A-1 film, a 45 nm thick compound A-3 film was formed thereon as a hole-transporting layer. On the A-3 layer, the compound 1 and compound D-2 were deposited in a film thickness ratio of 20:1 to form a 25 nm thick blue color emitting layer. On the thus formed emitting layer, compound ET-2 was deposited in a thickness of 25 nm as the electron-injecting layer. Subsequently, LiF was deposited in a thickness of 1 nm, followed by deposition of aluminum in a thickness of 150 nm to form a metal cathode, whereby an organic EL device was fabricated.

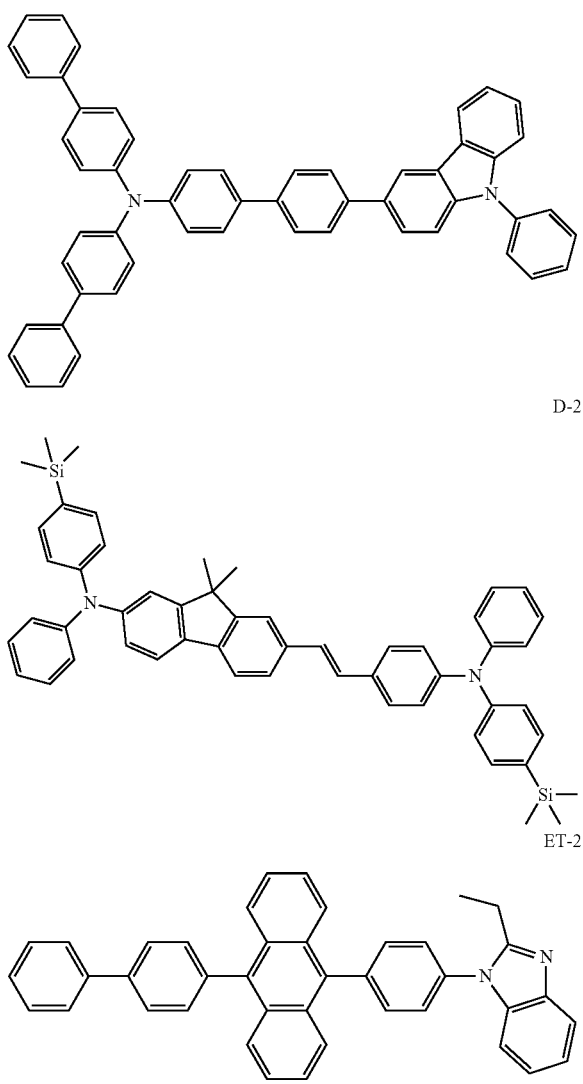

For the thus fabricated organic EL device, the voltage at the time of driving at a current density of 10 mA/cm$^2$, the external quantum yield, the chromaticity, and a half life at an initial luminance of 500 cd/m$^2$ were measured. The results are shown in Table 2.

Examples 13 to 16 and Comparative Examples 5 and 6

An organic EL device was fabricated and evaluated in the same manner as in Example 12, except that materials shown in Table 2 are used as a host and dopant of the emitting layer. The results obtained are shown in Table 2.

TABLE 2

| | Host | Dopant | Voltage (V) | Chromaticity CIEx | CIEy | EQE (%) | Lifetime (h) |
|---|---|---|---|---|---|---|---|
| Example 12 | Compound 1 | D-2 | 3.3 | 0.147 | 0.140 | 7.1 | 6200 |
| Example 13 | Compound 4 | D-2 | 3.3 | 0.147 | 0.127 | 7.6 | 6400 |
| Example 14 | Compound 7 | D-2 | 3.4 | 0.146 | 0.123 | 7.7 | 6300 |
| Example 15 | Compound 10 | D-2 | 3.3 | 0.148 | 0.114 | 6.8 | 6400 |
| Example 16 | Compound 11 | D-2 | 3.2 | 0.147 | 0.138 | 6.6 | 5100 |
| Com. Example 5 | H-1 | D-2 | 3.4 | 0.148 | 0.155 | 5.9 | 1700 |
| Com. Example 6 | H-3 | D-2 | 3.9 | 0.149 | 0.180 | 6.0 | 2500 |

It is understood from Tables 1 and 2 that, as compared with a case where disubstituted pyrene is used, holes are injected from a hole-transporting layer to an emitting layer more easily if the pyrene derivative of the invention is used as a host material of the emitting layer. Thus, it is believed that it becomes possible to drive a device at a lower voltage.

An organic EL device using a known pyrene derivative or a known bispyrene derivative as a host is inferior in blue color chromaticity, while the compound of the invention can suppress the degradation of chromaticity.

In addition, it is understood that an organic EL device using the pyrene derivative of the invention as a host material of an emitting layer has a long life. Although it has been believed that it is difficult to achieve both high color purity and long lifetime, the pyrene derivative of the invention can achieve both of them. Thus, the pyrene derivative of the invention is more suitable for a host which has high blue color purity and a long lifetime.

As mentioned above, the pyrene derivative of the invention is the most suitable host material for a blue color organic EL device which can allow a low-voltage driving, suppress the degradation of chromaticity, and has a long lifetime.

INDUSTRIAL APPLICABILITY

The pyrene derivative of the invention can be preferably used as a host material for an organic EL device. The organic EL device of the invention is useful as a light source for a planar emitting body of a wall television or backlight of a display.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The documents described in the specification are incorporated herein by reference in its entirety.

The invention claimed is:

1. An organic electroluminescence device, comprising a pair of electrodes and an organic compound layer therebetween, said organic compound layer comprising an emitting layer, wherein:

the emitting layer comprises a pyrene derivative represented by formula (1), such that a content of the pyrene derivative in the emitting layer is 50 to 100 wt %:

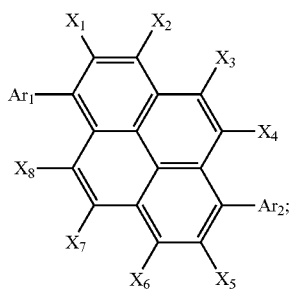

(1)

Ar₁ and Ar₂ are independently a substituted or unsubstituted aryl group having 6 to 30 ring carbon atoms;

X₁ and X₃ to X₈ are a hydrogen atom;

X₂ is a substituted or unsubstituted aryl group having 6 to 30 ring carbon atoms, provided that Ar₁ or Ar₂ is different from X₂; and in a case where any of Ar₁, Ar₂, and X₂ is the aryl group having a substituent, the substituent is independently an alkyl group, a cycloalkyl group, an aryl group, a silyl group, or a cyano group.

2. The organic electroluminescence device of claim 1, wherein Ar₁ and Ar₂ are independently a substituted or unsubstituted phenyl group.

3. The organic electroluminescence device of claim 2, wherein the substituted phenyl group is represented by formula (2):

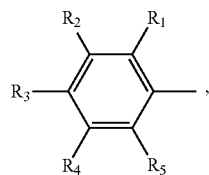

(2)

wherein:

R₁ to R₅ are independently a hydrogen atom or a substituent; and at least one of R₁ to R₅ is a substituted or unsubstituted aryl group having 6 to 30 ring carbon atoms.

4. The organic electroluminescence device of claim 3, wherein the substituent represented by formula (2) is a substituted or unsubstituted 2-biphenyl group.

5. The organic electroluminescence device of claim 1, wherein Ar₁ and Ar₂ are independently a substituted or unsubstituted 1-naphthyl group.

6. The organic electroluminescence device of claim 1, wherein Ar₁ and Ar₂ are independently a substituted or unsubstituted phenanthryl group.

7. The organic electroluminescence device of claim 1, wherein the emitting layer further comprises a dopant.

8. The organic electroluminescence device of claim 7, wherein the dopant is an aromatic hydrocarbon derivative.

9. The organic electroluminescence device of claim 7, wherein the dopant is an amine compound.

10. The organic electroluminescence device of claim 1, wherein X₂ is a substituted or unsubstituted naphthyl group, a substituted or unsubstituted phenanthryl group or a substituted or unsubstituted fluorenyl group.

11. The organic electroluminescence device of claim 1, wherein Ar₁ and Ar₂ are independently a substituted or unsubstituted phenyl group, a substituted or unsubstituted naphthyl group or a substituted or unsubstituted biphenyl group.

* * * * *